(12) United States Patent
Cantrell (10) Patent No.: US 7,374,745 B2
(45) Date of Patent: May 20, 2008

(54) ULTRASOUND CONTRAST AGENTS (75) Inventor: Gary L. Cantrell, Troy, IL (US)

(73) Assignee: Mallinckrodt, Inc., St. Louis, MO (US)

( * ) Notice: Subject to any disclaimer, the term of this patent is extended or adjusted under 35 U.S.C. 154(b) by 487 days.

(21) Appl. No.: 10/798,486

(22) Filed: Mar. 11, 2004

(65) Prior Publication Data
US 2004/0170565 A1 Sep. 2, 2004

Related U.S. Application Data (63) Continuation of application No. 09/806,680, filed as application No. PCT/US99/23685 on Oct. 12, 1999, now abandoned.

(60) Provisional application No. 60/103,860, filed on Oct. 12, 1998.

(51) Int. Cl.
A61B 8/00 (2006.01)

(52) U.S. Cl. ....................... 424/9.52; 424/9.5

(58) Field of Classification Search ............... 424/9.52, 424/9.5, 9.51, 489; 600/458
See application file for complete search history.

(56) References Cited

U.S. PATENT DOCUMENTS

| | | |
|---|---|---|
| 4,265,251 A | 5/1981 | Tickner |
| 4,316,391 A | 2/1982 | Tickner |
| 4,442,843 A | 4/1984 | Rasor et al. |
| 4,466,442 A | 8/1984 | Hilmann et al. |
| 4,483,345 A | 11/1984 | Miwa |
| 4,657,756 A | 4/1987 | Rasor et al. |
| 4,681,119 A | 7/1987 | Rasor et al. |
| 4,684,479 A | 8/1987 | D'Arrigo |
| 4,900,540 A | 2/1990 | Ryan et al. |
| 5,141,738 A * | 8/1992 | Rasor et al. ............... 424/9.52 |
| 5,352,436 A | 10/1994 | Wheatley et al. |
| 5,536,490 A | 7/1996 | Klaveness |
| 5,573,751 A | 11/1996 | Quay |
| 5,585,112 A | 12/1996 | Unger et al. |
| 5,614,169 A | 3/1997 | Klaveness et al. |
| 5,656,211 A | 8/1997 | Unger et al. |
| 6,045,777 A | 4/2000 | Church et al. |

FOREIGN PATENT DOCUMENTS

| | | |
|---|---|---|
| DE | 3834705 A1 | 12/1990 |
| EP | 0122624 B1 | 9/1988 |
| EP | 0123235 B1 | 9/1988 |
| EP | 0231091 B1 | 3/1993 |
| WO | WO 96/39197 A1 | 12/1996 |

* cited by examiner

Primary Examiner—Michael G Hartley
Assistant Examiner—Leah Schlientz
(74) Attorney, Agent, or Firm—Thompson Hine LLP (57) ABSTRACT New ultrasound contrast agents that comprise microbubbles encapsulating a gas within a shell made from a blend of bipolar compounds having mixed carbon chain length. The compounds have hydrophobic groups selected from the group consisting of straight-chained alkyls, alkylethers, alkylthioethers, alkyldisulfides, polyfluoroalkyls, and polyfluoroalkylethers having a carbon chain length greater than or equal to 16 and less than or equal to 32. The polar groups are connected to the hydrophobic groups by means of a linker. The polar head groups are selected from the group consisting of $CO_2\text{-}M^+$, $SO_3^-M^+$, $SO_4^-M^+$, $PO_3^-M^+$, $PO_4^-M^+_2$, $N(R)_4^+$, a pyridinium or substituted pyridinium group, and a zwitterionic group; R is selected from the group consisting of —H, —$CH_3$, alkyl, cycloalkyl, substituted cycloalkyls containing one or more heteroatoms, and benzyl and can be the same or different; and Z' is a nonionic and M is a cation.

9 Claims, 3 Drawing Sheets

ULTRASOUND CONTRAST AGENTS

APPLICATION CROSS-REFERENCE

This application is a continuation application of prior U.S. patent application Ser. No. 09/806,680 filed on Apr. 3, 2001, now abandoned which is a national phase application under 35 U.S.C. Section 371 of International Application No. PCT/US99/23685 filed Oct. 12, 1999, which claims benefit of U.S. Provisional Patent Application No. 60/103,860, filed Oct. 12, 1998.

BACKGROUND OF THE INVENTION

Ultrasound contrast is a very useful and widely used medical diagnostic technique. The technique takes advantage of the fact that the various fluids and tissues in the body reflect sound waves differently. This results in a contrast between reflected waves that can be detected and used to form an image of the tissue. Ultrasound is used for many different diagnostic purposes, e.g., prenatal imaging or to image bloodflow in the heart and arteries and observe blockages in blood circulation.

It has been discovered that an ultrasound image can be greatly enhanced by the presence of ultrasound contrast agents. By placing such contrast agents within the tissue to be imaged, a greater difference in the reflectance of the sound waves between the tissue to be imaged and the surrounding tissue occurs. This allows much sharper delineation of tissue boundaries and perfusion to be observed.

Such contrast agents are based on the acoustic impedance mismatch between a gas and a liquid. These agents are typically micron-sized bubbles containing various gases encapsulated in polymers, surfactants, proteins, polyaminoacids and their derivatives, liposomes, or inorganic shells. The bubbles, often called "microbubbles", are typically smaller than 10 micrometers so that they will pass through small vessels such as the capillary bed of the lung and reach the heart. They are commonly filled with a gas because it has been found that these gas-filled microbubbles provide very efficient ultrasound contrast, much better than that observed using liquid or solid contrast particles of equivalent size.

Although non-encapsulated gas microbubbles may be used for some purposes, they tend to change size very rapidly. The larger non-encapsulated gas microbubbles grow while the smaller microbubbles continue to diminish in size. Those that are small enough to pass through the lungs are effectively to small and dilute to provide useful contrast upon reaching the heart and are thus not practical for imaging the left side of the heart. The rate at which microbubbles undergo this type of change depends upon the actual gas used. Less soluble and diffusive types of gas will form non-encapsulated microbubbles that may be usable for imaging the left side of the heart.

Several encapsulated contrast agents have already been developed and are widely used. U.S. Pat. No. 5,614,169 describes microbubbles comprising carbohydrates and amphiphilic $C_{22-50}$ organic acids. The organic acids were described as preferably containing at least one carboxyl group and could be, e.g., straight chain fatty acids. U.S. Pat. No. 5,352,436 describes microbubbles which are stabilized by the presence of two different surfactants. The first surfactant tends to be substantially soluble and nonionic, examples being polyoxyethylene fatty acid esters, such as polyoxyethylene sorbitan monolaurate, polyoxyethylene sorbitan monopalmitate, polyoxyethylene sorbitan nonostearate, polyoxyethylene sorbitan tristearate, polyoxyethylene sorbitan monooleate and mixtures thereof. These esters include TWEEN 20, TWEEN 40, TWEEN 60, TWEEN 65 and TWEEN 80. The second surfactant is preferably insoluble and nonionic. These include sorbitan fatty acid esters, such as sorbitan monostearate, sorbitan monopalmitate and mixtures thereof. Such mixtures include SPAN 40 and SPAN 60, which comprise palmitic acid, myristic acid and pentadecanoic acid, and stearic acid, palmitic acid and myristic acid, respectively. Published PCT patent application WO 96/39197 describes stabilized ultrasound compositions comprising fluorinated amphiphilic compounds wherein these compounds can comprise short to long chain alkyls or fluoroalkyls.

Other patents have also described the use of sugars in ultrasound contrast agents. These include U.S. Pat. Nos. 4,681,119, 4,442,843 and 4,657,756 which disclose the use of particulate solids having a plurality of gas-filled voids and preferably also a plurality of nuclei for microbubble formation. EP-A-0123235 and EP-A-0122624 suggest ultrasound contrast agents consisting of surfactant-coated or surfactant-containing gas-containing microparticles which may include a variety of sugars. DE-A-3834705 suggests the use of suspensions containing microparticles of mixtures of at least one C10-20 fatty acid with at least one non-surface active substance, including sugars such as cyclodextrins, monosaccharides, disaccharides or trisaccharides, as well as other polyols and inorganic and organic salts.

Microbubbles have also been encapsulated in gelatin and albumen. ALBUNEX® Contrast Agent is a suspension of stable microencapsulated air bubbles which are encapsulated in human serum albumin. OPTISON® Contrast Agent is a suspension of stable microencapsulated octafluoropropane bubbles which are encapsulated in human serum albumin. Both are prepared by sonicating dilute human albumin at a temperature slightly below denaturing. ALBUNEX is prepared by sonicating in the presence of air; OPTISON® in the presence of octafluoropropane. Both are composed of gas-filled microbubbles with a mean diameter in the range of 3-5 microns and stabilized by a thin albumin shell.

U.S. Pat. No. 4,684,479 discloses surfactant mixtures for the production of stable gas-in-liquid emulsions comprising: (a) a glycerol monoester of saturated carboxylic acids containing from about 10 to about 18 carbon atoms or aliphatic alcohols containing from about 10 to about 18 carbon atoms; (b) a sterol-aromatic acid ester; and (c) a sterol, terpene, bile acid or alkali metal salt of a bile acid.

U.S. Pat. No. 4,466,442 discloses a solution for the production of gas microbubbles which contains a solution of at least one tenside and at least one viscosity-raising compound. Examples of suitable non-ionic tensides include polyoxyethylene fatty acid esters, and polyoxyethylated sorbitan fatty acid esters. Examples of viscosity-raising compounds include mono- or polysaccharides, dextrans, cyclodextrins, hydroxyethyl amylose, polyols, proteins, proteinaceous materials, amino acids, and blood surrogates.

U.S. Pat. No. 5,573,751 teaches the advantage of using any of a variety of gases in microbubbles which gases are longer lasting than other gases such as air. U.S. Pat. No. 5,352,436 teaches one process for preparing stabilized gas microbubbles with mean diameter less than 10 micrometers. U.S. Pat. No. 5,656,211 also teaches methods for preparing gas-filled microbubbles.

European Patent Application 0231091 discloses emulsions of oil in water containing highly fluorinated organic compounds as contrast agents. U.S. Pat. No. 4,900,540 describes the use of phospholipid-based liposomes containing a gas or gas precursor as a contrast-enhancing agent.

Ultrasound contrast agents have also been used for purposes other than tissue imaging, e.g., measuring pressure in a system or measuring fluid flow rates. U.S. Pat. No. 4,265,251 teaches a method of determining the pressure within a liquid containing vessel by (1) adding a solid precursor for at least one bubble the liquid, (2) retaining the precursor in the liquid for a sufficient time to form at least one bubble and to generate a sonic signal, (3) measuring a characteristic of the sonic signal which is representative of the pressure in the liquid, and (4) determining the pressure in the liquid from the measured characteristic. U.S. Pat. No. 4,483,345 teaches a method of non-destructively measuring the pressure of a desired region within a substance, from outside, by a process wherein ultrasonic waves are applied to the desired region within a substance, to generate bubbles within the liquid existing in the region during the negative pressure cycle of the ultrasonic waves and, thereafter, the generation of bubbles is detected by harmonic or subharmonic ultrasonic waves which accompany such bubbles and/or by the echo of other ultrasonic waves of higher frequency applied to the region. U.S. Pat. No. 4,316,391 teaches a method of measuring fluid flow rate in a system having a conduit through which a fluid flows. The method comprises adding a substance which provides a plurality of bubbles of a known quantity and size to the system upstream of the conduit. A sonic pulse is generated from a position opposite and spaced from the conduit as the bubbles pass through the conduit. Reflected sonic images are measured, which images are created by reflection of the pulse from the wall of the conduit distal from the position. Additionally, other reflections are measured from the bubbles themselves flowing between the two walls. The fluid flow rate is then determined from the sonic images.

A variety of methods are used to make microbubbles. Several of these are outlined in published PCT application WO 96/39197. This same application also describes many of the gases which may be included within the microbubbles.

These known agents are satisfactory for some applications but have limitations that prevent them from being useful for many purposes. They are often not stable when subjected to sterilization procedures and have relatively short half-lives after formulation or reconstitution. Also, the physical properties of the microbubbles at effective concentrations limit the depth in the tissue where a diagnostic image can be obtained. Often useful images can only be acquired for tissue a few centimeters from the ultrasound transmitter/receiver thus limiting the "penetration" of the procedure and the depth in the body from which images can be obtained. The amount of signal loss accountable to a variety of scattering processes is known as attenuation. Further, the physical properties of the microbubbles cause relatively high attenuation that limits the usefulness of the agent to obtain certain types of images, e.g. myocardial perfusion and images that must be obtained immediately after injection.

Additionally, known agents have not proven useful for measuring blood pressure in the body, particularly for measuring pressure within the cardiovascular system.

To illustrate these limitations, consider how an ultrasound image is obtained. An ultrasound image is obtained when an emitted sound wave strikes a microbubble and is reflected back to and detected by a receiver. Attenuation processes occur along the path transversed by the sound wave as it is returning to the receiver. Attenuation increases with the number and size of the microbubbles to which the transmitted signal interacts. Therefore, at some concentration for a given agent, image resolution and contrast is lost. Thus, the image detail deteriorates since many reflected signals no longer reach the receiver at the frequency of imaging. The depth of penetration by the signal is thus limited.

In addition, known ultrasound contrast agents are often administered to a patient by quickly injecting a large volume of the agent into the patient, i.e. a "bolus" injection. Ultrasound measurements are started immediately and taken over the next several seconds or minutes. However, the image obtained from the ultrasound measurement occurs in three stages. The measurement initially produces an image of relatively low diagnostic value as the microbubbles first enter the system. Next, as the concentration of the microbubbles increases, image contrast is lost due to the effects of attenuation. At this stage the image appears to "darken" to a point where virtually no image can be obtained. This shadowing is principally due to attenuation of the ultrasound signal caused by the high concentration of the contrast agent. The numerous microbubbles scatter or translate the reflected signal and prevent it from reaching the receiver. Then, in the third stage, the faded image returns as attenuation abates with a decline in the concentration of the contrast agent due to dilution, destruction, and uptake processes in the imaged organism. Diagnostic imaging is usually carried out in this often brief third stage.

The problem is that in the second stage regions which contain a large number of microbubbles obscure adjacent farfield locations of key medical interest. These adjacent locales often contain relatively much less contrast agent at peak dose. As the overall concentration declines and the image returns, the amount of contrast remaining in these areas of interest is insufficient or sub-optimal for giving good contrast or flow information. For example, myocardial perfusion tests using known contrast agents give poor results, if at all. The high concentration of contrast agent in the heart chambers following a bolus injection initially attenuates the signal obscuring the image of the perfusion of the heart muscle. As the concentration of contrast agent in the blood declines, the attenuation diminishes but little or no contrast enhancement of the heart muscle remains. Similarly, when measuring heart muscle function in a stress test, the patient is "stressed" and the ultrasound image is taken immediately before the patent's heart rate declines. Known ultrasound contrast agents are of limited use during a stress test because the imaging is carried out when these agents are in the second or "attenuated" stage. By the time the image returns, the heart rate is off peak and the image is no longer diagnostic.

Therefore, there is a need for ultrasound contrast agents that are more stable generally than known agents, that permit greater signal penetration than known agents by lowering attenuation, and that are useful in procedures where known agents have limited applicability. Such agents must be highly efficient. They must be very reflective yet minimally attenuating so that imaging procedures can produce better and more consistent ultrasound images, particularly for imaging heart perfusion, measuring blood pressure, and similar procedures.

SUMMARY OF THE INVENTION

The present invention relates to the field of ultrasound imaging and particularly to the development of novel ultrasound contrast agents in the form of microbubbles that have new and useful ultrasound characteristics.

It is, therefore, an object of the present invention to provide ultrasound contrast agents that are simple to prepare, stable during the preparation process, and stable during storage.

It is another object of the present invention to provide ultrasound contrast agents that have minimal attenuation and therefore permit greater signal penetration than known agents.

It is another object of the present invention to provide ultrasound contrast agents that are useful in imaging procedures that require a diagnostic image to be taken immediately after administration of the agent.

It is another object of the present invention to provide ultrasound contrast agents that are useful for purposes other than tissue imaging, e.g., measuring pressure in a system or measuring fluid flow rates.

It is a further object of the present invention to provide ultrasound contrast agents that are useful in imaging myocardial perfusion and a method for imaging myocardial perfusion.

It is another object of the present invention to provide ultrasound contrast agents that are useful for measuring blood pressure and a method for measuring blood pressure in a patient, particularly in the heart.

These and other objects are achieved using new and structurally distinct ultrasound contrast agents that comprise microbubbles encapsulating a gas within a shell made from compounds having the following structure: $R_1$—X-Z; $R_2$—X-Z; and $R_3$—X-Z', where $R_1$, $R_2$ and $R_3$ are hydrophobic groups selected from the group consisting of straight-chained alkyls, alkylethers, alkylthiolethers, alkyldisulfides, polyfluoroalkyls, and polyfluoroalkylethers having a carbon chain length greater than or equal to 16 and less than or equal to 32 and where $R_1$ is greater than $R_2$ and $R_1$ is greater than or equal to $R_3$; $R_3$ has one or more such hydrophobic groups having the same or different lengths; X is a linker connecting the hydrophobic group to the polar head group; Z is a polar head group selected from the group consisting of $CO_2\text{-}M^+$, $SO_3^-M^+$, $SO_4^-M^+$, $PO_3^-M^+$, $PO_4^-M^+_2$, $N(R)_4^+$, a pyridinium or substituted pyridinium group, and a zwitterionic group; R is selected from the group consisting of —H, —$CH_3$, alkyl, cycloalkyl, substituted cycloalkyls containing one or more heteroatoms, and benzyl and can be the same or different; and Z' is a nonionic group.

The microbubbles made using the above compounds are useful as ultrasound contrast agents in diagnostic and therapeutic medical procedures because they have exceptionally high reflectivity, have very low attenuation, and can exhibit large acoustic changes with frequency for only a slight pressure variation. They are stable during the manufacturing and sterilization process and are stable for long storage periods. Because of their inherit low attenuation, they can be administered in large doses and imaging can begin immediately after administration. Similarly, the low attenuation permits greater penetration by the signal and allows images to be acquired at greater depths in the tissue. The agents are particularly useful for procedures where the image is masked by attenuation with known agents, e.g., myocardial perfusion tests. These agents can be given in very high doses without using image quality.

Other objects, advantages, and novel features of the present invention will become apparent in the following detailed description of the invention.

DETAILED DESCRIPTION OF THE INVENTION

The present invention provides a composition useful as new and structurally distinct ultrasound contrast agents that comprise micron-sized microbubbles encapsulating a gas within a shell made from a blend of bipolar compounds having inter-molecular hydrophobic regions of mixed carbon chain length. The compounds have the following structure: $R_1$—X-Z; $R_2$—X-Z; and $R_3$—X-Z', where $R_1$, $R_2$ and $R_3$ are hydrophobic groups selected from the group consisting of straight-chained alkyls, alkylethers, alkylthiolethers, alkyldisulfides, polyfluoroalkyls, and polyfluoroalkylethers having a carbon chain length greater than or equal to 16 and less than or equal to 32 and where $R_1$ is greater than $R_2$ and $R_1$ is greater than or equal to $R_3$; $R_3$ has one or more such hydrophobic groups having the same or different lengths; X is a linker connecting the hydrophobic group to the polar head group; Z is a polar head group selected from the group consisting of $CO_2\text{-}M^+$, $SO_3^-M^+$, $SO_4^-M^+$, $PO_3^-M^+$, $PO_4^-M^+_2$, $N(R)_4^+$, a pyridinium or substituted pyridinium group, and a zwitterionic group; R is selected from the group consisting of —H, —$CH_3$, alkyl, cycloalkyl, substituted cycloalkyls containing one or more heteroatoms, and benzyl and can be the same or different; and Z' is a nonionic group.

$R_1$ and $R_2$ must have different carbon chain lengths. Preferably $R_1$ is at least two carbons longer than $R_2$ and most preferably $R_1$ is at least 4 carbons longer than $R_2$.

Preferably, $R_1$, $R_2$ and $R_3$ are straight-chained alkyl groups having from about 20 to 30 carbon atoms and $R_3$ is a single chained molecule. When $R_3$ has two or more carbon chains, they are preferably the same length but may have different lengths.

The bipolar compounds of the present invention have a hydrophobic group and a polar group that are connected by a linker. The compounds are preferably carboxylic salts, most preferably carboxylic salts of unbranched alkyl, alkylether, alkylthiolether, alkyltdithiolether, perfluoroalkyl, polyfluoroalkyl ether compounds. Long-chained acids useful for forming the hydrophobic group include eicosanoic acid ($C_{20}$), heneeicosanoic acid ($C_{21}$), docosanoic acid ($C_{22}$), tricosanoic acid ($C_{23}$), tetracosanoic acid ($C_{24}$), pentacosanoic acid ($C_{25}$), hexacosanoic acid ($C_{26}$), heptacosanoic acid ($C_{27}$), octacosanoic acid ($C_{28}$), nonacosanoic acid ($C_{29}$) and triacontanoic acid ($C_{30}$).

Long-chained alcohols useful for forming the hydrophobic group include eicosanol ($C_{20}$), heneeicosanol ($C_{21}$), docosanol ($C_{22}$), tricosanol ($C_{23}$), tetracosanol ($C_{24}$), pentacosanol ($C_{25}$), hexacosanol ($C_{26}$), heptacosanol ($C_{27}$), octacosanol ($C_{28}$), nonacosanol ($C_{29}$), and triacontanol ($C_{30}$).

Long-chained amines useful for forming the hydrophobic group include eicosylamine ($C_{20}$), heneeicosylamine ($C_{21}$), docosylamine ($C_{22}$), tricosylamine ($C_{23}$), tetracosylamine ($C_{24}$), pentacosylamine ($C_{25}$), hexacosylamine ($C_{26}$), heptacosylamine ($C_{27}$), octacosylamine ($C_{28}$), nonacosylamine ($C_{29}$), and triacontanylamine ($C_{30}$).

X can be any suitable linker capable of connecting the hydrophobic group to the polar head group. Preferably, X is selected from the group consisting of —$(CH_2)_m$—, —$(CH_2)_m$ $CO_2(CH_2)_n$—, —$(CH_2)_m CONH(CH_2)_n$—, —$(CH_2)_m NHCONH(CH_2)_n$—, —$(CH_2)_m OCONH(CH_2)_n$ —, —$(CH_2)_mO(CH_2)_n$—, —$(CH_2)_mNH(CH_2)_n$—, —$(CH_2)_m N[(CH_2)_m]_2$—, —$(CH_2)_mS(CH_2)_n$—, —$(CH_2)_m$—, —$(CH_2)_mSO(CH_2)_n$—, —$(CH_2)_mSO_2(CH_2)_n$—, —$(CH_2)_mNH(CH_2)_nCO_2(CH_2)_o$—, and —$[(CH_2)_m]_2N(CH_2)_nCONH(CH_2)_o$—, where m, n, and o are the same or different and are less than 5. Other useful linkers include DL-lysine, aspartic acid, glutamic acid, serine, cysteine, homocysteine, cystine, serinol, itaconic acid, tigilic acid, maleic acid, DL-malic acid, succinic acid, tartaric acid, malonic acid, citric acid, phthalic acid, terephthalic acid, and the common biological buffers N,N-bis[2-hydroxyethyl]-2-aminoethanesulfonic acid (BES), N,N-bis(2-hydroxyethyl) glycine (BICINE), 3-[N,N-bis(2-hydroxyethyl)amino]-2-hydroxypropanesulfonic acid (DIPSO), N-tris[hydroxylmethyl]methyl-3-aminopropanesulfonic acid (TAPS), and N-tris[hydroxylmethyl]glycine (TRICINE).

Z' can be any suitable nonionic group capable of binding to the linker and interacting with the environment outside the microbubble. Generally, Z' is selected from the group consisting of polysorbates, polyglycerols, polypeptides, polynucleotides, polysaccharides, polyvinylpyrrolidones, polyvinylalcohols, polyethyleneglycols, and composites thereof. When the polar group is poly(ethyleneglycol), the number of ethyleneglycol monomer units is greater than or equal to 20. Preferably, Z' is poly(ethyleneglycol)$_p$ with p between 40 and 150 units. Polyethyleneglycol methyl ether is the most preferred nonionic compound for the present invention.

The compounds containing $R_1$, $R_2$, and $R_3$ are mixed or blended together and processed using known techniques to form microbubbles useful as ultrasound contrast agents, e.g., methods of mixing such as sonication, microfluidization, ultramixing or colloid milling at temperatures greater than 25° C. in the presence of one or more gases in a biocompatible medium such as normal (0.9%) saline, glycerol/water, glucose/water, poly(ethyleneglycol)/water, sucrose/water, or 1,2-propandiol/water.

The compounds containing $R_1$ comprise from about 5 to about 30 percent by weight of the microbubble shell composition, the compounds containing $R_2$ comprise from about 5 to about 30 percent by weight of the microbubble shell composition, and the compounds containing $R_3$ comprise from about 40 to about 90 percent by weight of the microbubble shell composition. Preferably the composition comprises about 20 to 30 percent by weight $R_1$, about 20 to 30 percent by weight $R_2$, and about 40 to 60 percent by weight $R_3$.

In one set of preferred embodiments, polyethyleneglycol methyl ether is connected by a nitrogen or oxygen atom at the terminus to give the long-chained nonionic conjugate, $R_3$—X-Z' to from polyethyleneglycol methyl ether acid amides such as eicosamide ($C_{20}$), heneeicosamide ($C_{21}$), docosamide ($C_{22}$), tricosamide ($C_{23}$), tetracosamide ($C_{24}$), pentacosamide ($C_{25}$), hexacosamide ($C_{26}$), heptacosamide ($C_{27}$), octacosamide ($C_{28}$), nonacosamide ($C_{29}$), triacontanmide ($C_{30}$), and hentriacontanamide ($C_{31}$); polyethyleneglycol methyl ether esters such as eicosanoic acid ($C_{20}$), heneeicosanoic acid ($C_{21}$), docosanoic acid ($C_{22}$), tricosanoic acid ($C_{23}$), tetracosanoic acid ($C_{24}$), pentacosanoic acid ($C_{25}$), hexacosanoic acid ($C_{26}$), heptacosanoic acid ($C_{27}$), octacosanoic acid ($C_{28}$), nonacosanoic acid ($C_{29}$), triacontanoic acid ($C_{30}$), and hentriacontanoic acid ($C_{31}$); and polyethyleneglycol methyl ether alkylethers such as eicosanyl ($C_{20}$), heneeicosanyl ($C_{21}$), docosanyl ($C_{22}$), tricosanyl ($C_{23}$), tetracosanyl ($C_{24}$), pentacosanyl ($C_{25}$), hexacosanyl ($C_{26}$), heptacosanyl ($C_{27}$), octacosanyl ($C_{28}$), nonacosanyl ($C_{29}$), triacontanyl ($C_{30}$), and hentriacontanyl ($C_{31}$).

In a preferred embodiment, the microbubbles comprise docosanoic acid salts and octacosanoic acid salts in equal weight amounts. Preferably, the compound containing $R_3$ comprises docosamide polyoxyethylene[120] methyl ether in an amount equal or greater to the sum of the weight of the other two compounds. In another preferred embodiment, the microbubbles comprise docosanoic acid salts and triacontanoic acid salts in equal weight amounts. Preferably, the compound containing $R_3$ comprise docosamide polyoxyethylene[120] methyl ether in an amount equal or greater to the sum of the weight of the other two compounds.

The microbubbles of the present invention contain one or more gases. Preferably the gas is insoluble in water and is selected from the group consisting of sulfur hexafluoride, tetrafluoromethane, hexafluoroethane, octafluoropropane, decafluorobutane, dodecafluoropentane, perfluorohexane, or mixtures thereof. The gas can also be formed from these gases or gas mixtures and common gases such as nitrogen, oxygen, helium, neon, argon, xenon, carbon dioxide, or mixtures thereof.

The microbubbles of the present invention may contain other optional components such as stabilizers and adjuncts for adjusting or modifying the properties of the formulation such as ionic strength, osomolity, viscosity. Soluble modifiers include but are not limited to sodium chloride, sucrose, lactose, glucose, galactose, dextrose or other carbohydrates, glycerol, polysaccharides such as hyaluronic acid, chondroitin, heparin, keratan, dextran, gelatin, agar, agarose, cellulose, and antioxidants such as ascorbic acid and citric acid.

The microbubbles made from the above compounds have exceptionally high reflectivity while exhibiting very low attenuation. They are stable during the manufacturing process, including sterilization procedures at elevated temperatures and pressure, and stable over long storage periods, i.e., have a long shelf-life. Because of the low attenuation, they can be administered in large doses and images can be taken immediately after administration. Similarly, the low attenuation permits greater penetration by the signal and allows images to be taken at greater depths in the tissue.

The microbubbles are particularly useful for procedures where the image is masked by attenuation with known agents, e.g., myocardial perfusion tests. In general, the microbubbles can be optimized for a chosen frequency range. In particular, cardiac perfusion is observed at 2 megahertz and above with little loss due to attenuation at low to high doses of the microbubbles.

The ultrasound contrast agents are generally used to obtain an ultrasound image of body tissue. The agents are inserted into the body and an ultrasound image is taken by conventional means. The superior properties of the agents provide an improved image when compared to known agents.

The ultrasound contrast agents can also be used for purposes other than tissue imaging, e.g., measuring pressure in a system or measuring fluid flow rates. The microbubbles have properties that permit large acoustic changes with frequency for only a slight pressure variation. This makes them useful for measuring pressure differentials in a closed system such as the body circulatory system, particularly for blood pressure changes in the heart. The agents are inserted into the system and the acoustic changes are measured. If the pressure in the system has changed, the acoustic properties will change in proportion and the change in pressure or fluid flow rate can easily be calculated.

Therefore, the present invention provides a method for taking ultrasound images of tissue at greater depths than know methods. The high reflectivity combined with the very low attenuation characteristic of the present microbubbles give excellent images at doses which in comparison to known agents would totally obscure the image and prevent any tissue penetration.

The present invention also provides a method for imaging myocardial perfusion. The agent is administered to the patient and an ultrasound image taken immediately. Because the agent has low attenuation, the high concentration of agent in the heart does not mask the signal from the myocardial tissue during the "darkening" stage typical of known agents, even at high doses of the present agent.

Further, the present invention provides a method useful for measuring pressure changes in a closed system, preferably intra-arterial pressure changes. Within in a particular frequency range, the microbubbles of the present invention have been shown to exhibit larger acoustic changes in response to minor pressure variations than agents with more conventional shell compositions or no shell at all. The large shift in attenuation can be quantitatively measured and correlated much more accurately than the little if any shift shown by other agents. Therefore, the microbubbles can be used to remotely sense pressure. Also, even without quantitative attenuation measurement technology, the large shift in attenuation permits the clinician to assess qualitatively the presence of dangerously elevated right-heart intracardiac pressures by simply observing the image using the following procedure. Early in the washout from a bolus intravenous or intra-arterial injection, the pressure-sensitive microbubbles of the present invention will exhibit high attenuation over a particular range of frequencies. This is evidenced by an easily visualized darkening of the image in the left ventricle of the heart during systole. A normal right ventricle exhibits much lower pressures than the left ventricle and therefore does not cause the same amount of attenuation over the same frequency range, i.e., darkening of the image. If the right ventricle exhibits substantial darkening, this indicates excessive right heart pressures associated with disease, e.g., pulmonary hypertension. The clinician uses the darkening in the left ventricle for comparison. Right ventricular darkening of the same amount as the left ventricle at a particular point in the cardiac cycle indicates that the right ventricular pressure is approximately the same as in the left ventricle—a dangerously high pressure. Use of the present agents avoids invasive procedures such as cardiac catheterization, an expensive, highly invasive and dangerous diagnostic procedure.

The microbubbles of the present invention are also useful for purposes other than tissue imaging, e.g., measuring pressure in a non-bodily system or measuring fluid flow rates. When samples of these type agents were diluted into aqueous media contained in a sealed flexible container, large reversible darkening of the ultrasound image with depth of field was observed with only minor pressure changes on the outside of the container. Small pressure changes can thus be calibrated against the large attenuation changes in the transmitted and reflected signal. A simple ultrasound transducer in conjunction with these chemically compatible microbubbles can serve as a remote pressure monitor. Applications in which this invention applies include but are not limited to monitoring feedlines into reactors or vessels, reaction vessels, extravasation of infusions into the body.

Figure 1:
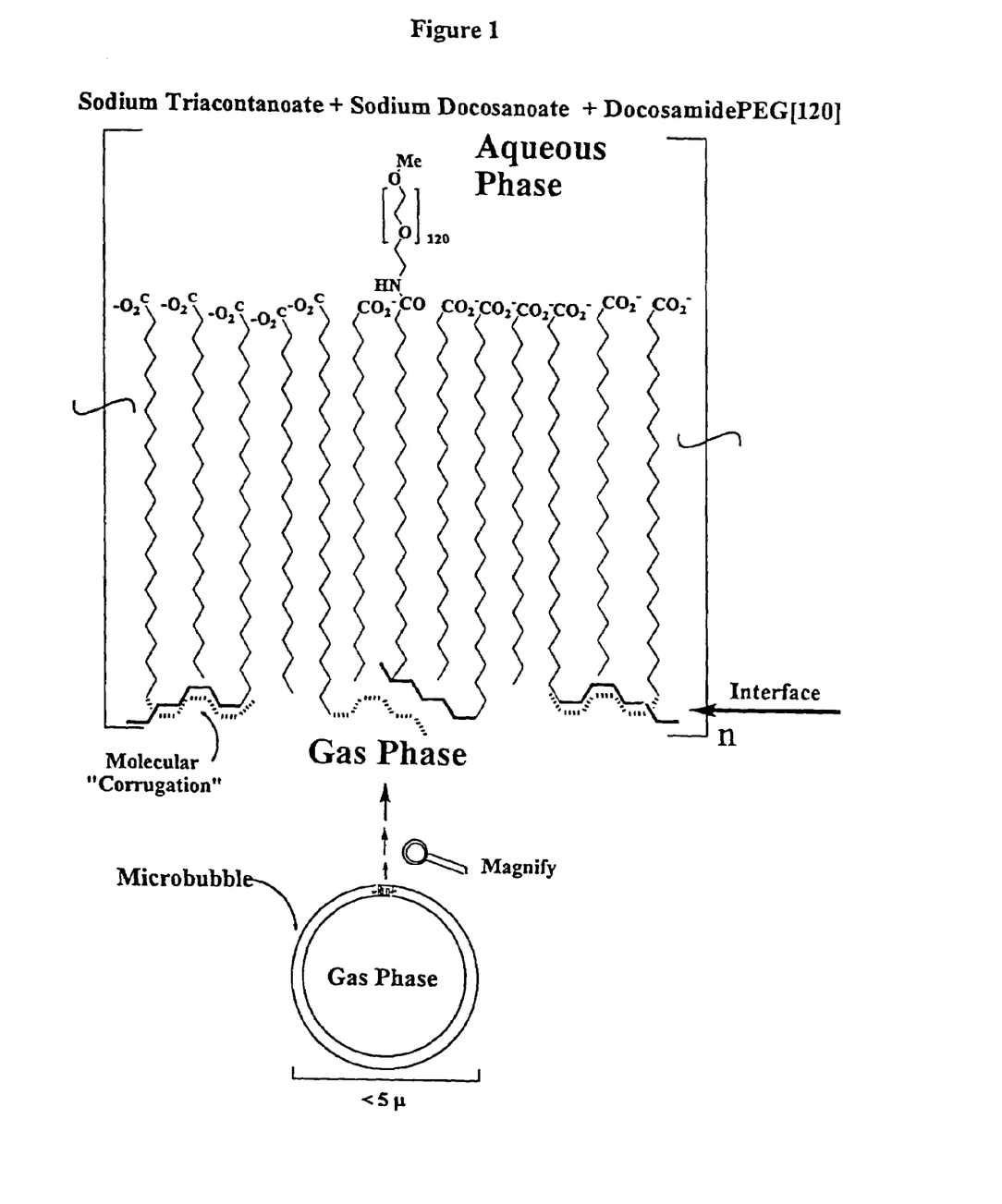
FIG. 1 shows a 2-dimensional representation of the three dimensional microbubble structure and illustrates how the longer carbon chains are believed to assemble beneath the shorter carbon chains to form a wall of "molecular corrugation."

Without being bound by any theory, it is believed that the enhanced stability of the present invention is due to the longer carbon chains assembling beneath the shorter carbon chains because of the interaction with the gas that is encapsulated and the enhanced properties are due to a "stiffer" shell formed by such wrapping. FIG. 1 shows a 2-dimensional representation of the three dimensional microbubble structure and illustrates how the longer chain is believed to arrange underneath the shorter chain and provide the enhanced properties of the present invention.

Those of skill in the art will recognize that many variations of combinations of compounds may be mixed to yield useful contrast agents which fall within the scope of this invention. The following Examples illustrate some of these contrast agents and are not meant to be totally inclusive of the possibilities envisaged by the invention.

Experimental Methods and Equipment

The data from the examples given below was obtained using the physical, in vitro and in vivo protocols and methods described herein and the equipment listed below.

Equipment: $^1$H & $^{13}$C NMR was carried out using a Varian Gemini 300 MHz spectrometer. Infrared spectra were recorded on a Nicolet MagnaIR™ 550 spectrometer. Silica gel thin chromatography plates were purchased from Analtech, Inc. of type GF of 250 micron thickness.

Size Distribution and Concentration Determinations: Particle counting was performed in a Coulter™ Multisizer II Instrument. The instrument was calibrated and validated at the specified time intervals as stated for its use. Samples were diluted by transferring 20 µL of agent into 200 mL of Isoton® II (Coulter Co.) as the electrolyte solution. The micropipette tip opening was located 5 mm under the electrolyte surface with the stirrer at a setting of 2.5. The volume of the injected material was entered into the Coulter™ Multisizer II level 2.1 software. The amount of sample injected was chosen in order not to overload the instrument and to have coincidence correction factor under 0.3. The amount of the injected material was reduced until the agreeing size distributions were obtained. Five seconds after the injection, the valve of the instrument was placed from "RESET" to "COUNT" position, and counting was started automatically according to the program. Counting data file was transferred to the IBM PC-compatible computer running MS-DOS Windows 3.0 with the Coulter Data Acquisition program. Number and volume distribution plots, the particle concentration, total particle volume and mean size were calculated by the software.

In Vitro Protocols for Acoustic Characterization

Methods: The suspension was mixed thoroughly and continuously during measurement to ensure a random, homogeneous spatial distribution of microbubbles. Finally, the power of the insonifying transducer was kept low enough to ensure that microbubbles were not destroyed during measurement. A special measurement system was designed and constructed to address these issues.

Specimen Chamber: The specimen chamber that held the agent during insonation was an important element of the measurement system. A micropipette was inserted through a large threaded hole in the chamber and was used to introduce the desired amount of the agent into the 8.5 mL of Isoton® II (a saline solution containing buffers) in the chamber. This suspension and Isoton® II was contained within the main body of the chamber, which was approximately 50 mm in diameter and 4.0 mm thick. The walls were made of Saran Wrap™, and serve as acoustic windows. Once the agent has been introduced, the suspension was continuously mixed using a micropipette set to 64 µL as described below.

Chamber Dosing Procedure: A rigorous material handling procedure was developed to optimize measurement repeatability. Each experiment consisted of measurements of suspensions of an agent at specific concentrations. Before each experiment, the agent in a vial was placed on a roller mixer and allowed to warm to room temperature. The desired amount of agent (1 to 255 µL) was withdrawn using a micropipette. The vial was then closed and placed back on the roller mixer. The pipetted volume was delivered into the specimen chamber containing 8.5 mL of Isoton® II at 37.5° C. The chamber was quickly placed into a 37.5° C. water tank, and the suspension was pipette-agitated during the course of the measurement. The measurement took approximately 20 seconds to complete, after which the chamber was rinsed with deionized water and re-dosed with 37.5° C. Isoton® II. This procedure was repeated for each concentration investigated.

Experimental Setup and Acquisition: The measurements were performed using a pair of broadband immersion PVDF transducers (0.4" diameter, 3.25" focal length Panametrics model ZF3002-SU). The transmitting transducer was excited using a square wave pulser system, which yields broadband (1 to 20 MHz), approximately unipolar pulses. The square wave pulser also permitted fine adjustments of the energy being delivered to the suspension of agent. The insonifying energy was an important factor to be able to control, as nonlinear effects (such as second harmonics and microbubble destruction) become increasingly important as the input power rises.

The transducers were placed roughly 6" apart, and the sample chamber was placed midway between them during measurement. Two different protocols were followed for backscatter and attenuation measurements. For attenuation measurements, the transmitted pulse passed through the suspension and was received by the receiving transducer. The signal then passed through a broadband receiver for amplification (Panametrics 5800) and was digitized at 250 mega-samples per second by a digitizing oscilloscope (Gage CS2125). Five sets of one thousand traces were digitized and averaged together and then stored for later analysis. This analysis required one reference trace, which was acquired by averaging 1000 traces from a specimen chamber having only Isoton® II. For backscatter measurements, the signal was reflected back to the transmitting transducer and then passed through a broadband receiver for amplification (Panametrics 5800) and was then digitized at 250 mega-samples per second by a digitizing oscilloscope (Gage CS2125). 500 RF traces were acquired (at a rate of approximately 30 traces per second) for each dilution. These traces were stored to disk for later analysis. 500 Reference traces were also acquired using a stainless steel reflector.

During acquisition, the suspension was continuously mixed using a micropipette. The volume of the micropipette was set to 64 µL and its tip inserted into the chamber so that approximately 1 mm of the tip was visible inside the chamber. This configuration insured that the tip did not interfere with the ultrasound beam.

The measurements proceeded according to the following steps: (1) the tank operator dosed the chamber and placed it in the specimen chamber holding sled in the water bath; (2) the tank operator steadied the specimen chamber in the sled with their left hand and operated the mixing pipette with their right hand; (3) when the measurement was over, the tank operator removed the chamber and rinsed the chamber with deionized water; and (4) next, the tank operator re-dosed the chamber and repeated the steps above.

In vivo Protocols for Acoustic Characterization

Dogs were anesthetized with an intravenous injection of sodium thiopental (20 mg/kg at 20 mg/mL). Upon completion of induction, each dog was incubated and the cuff of the endotracheal tube inflated. The endotracheal tube was attached to the Drager anesthetic apparatus. Anesthesia was maintained by either spontaneous inhalation or mechanical ventilation with 0.5 to 3.0% isoflurane using compressed air as the carrier gas. The oxygen content of the inhaled gas was maintained at an $FiO_2$ of 20±2, using supplemental oxygen as needed.

A cannula filled with heparinized saline (20 U/mL) was inserted into a femoral artery for measurement of blood pressure. A second cannula was placed in the opposite femoral artery to facilitate sampling of the arterial blood for measurement of blood gases. A Swan-Ganz catheter was inserted into the jugular vein and advanced into the pulmonary artery to measure arterial pressures and cardiac output.

Needle electrodes were placed on and under the skin of the right forelimb and left hind-limb to obtain lead II electrocardiograms (ECG). Heart rate data was recorded on videotape.

A pulse oximetry probe (Model 340 Pulse Oximetry, Palco Labs, Santa Cruz, Calif.) was placed on the tongue of the animal for monitoring oxygen saturation of the arterial blood.

Blood pressure and ECG data was collected continuously by a Modular Instruments Incorporated data acquisition system. Raw waveforms were stored on a Core WORM (write Once Read Many) optical disk system. Blood pressures were collected at 256 Hz and the ECG was acquired at a rate of 512 Hz. Blood pressures and heart rate were observed during the course of the experiment.

Arterial blood samples were obtained prior to each group of contrast injections. These specimens analyzed for $PO_2$ and $PCO_2$ content immediately after collection using a Ciba Corning 238 pH/Blood Gas Analyzer (Ciba Corning Diagnostics Corp., Medfield, Mass.).

Hair was shaved from the ventral portion of the thorax and, in some cases, the abdomen.

Two-dimensional short axis images of the heart were collected using as 5 MHz phase array transducer coupled to a Hewlett-Packard Sonos 500 ultrasound instrument.

The gain and power settings for the ultrasound system were adjusted to obtain optimal image enhancement with contrast at the beginning of the experiment and thereafter left unchanged.

Baseline images of the heart were obtained before administration of the contrast material. Images were collected continuously for approximately 30 seconds before, during and for at least one minute after injection of the test substance.

Prior to the administration of the agent, the angiocatheter and extension tubing was flushed with 3.0 mL of heparinized saline.

Test materials were injected at an initial dose-volume of 50 mL. Subsequent injections of the test material were at higher or lower dose-volumes depending on the contrast produced by the first injection. Dose-volumes changed in a logarithmic fashion. A stabilization period of at least three minutes was observed between injections.

Initially, an angiocatheter (18 gauge) was placed in the cephalic vein for administration of contrast media. The angiocatheter was attached to a short connector tube and a three-way stopcock; all of which were filled with heparinized saline (20 U/mL).

Arterial blood samples were collected approximately every 30 to 60 minutes. These specimens were analyzed for the amount of dissolved oxygen and carbon dioxide.

At the completion of the experiment, end diastolic images (baseline, peak, 5th, 10th, 15th, 20th, 25th and 30th after contrast enters the left ventricle) were captured and digitized from videotape. The captured images were analyzed by video densitometry. Region of interest analysis was performed on an area within the left ventricular chamber.

The mean and standard error of the mean was calculated for the video densitometry data for each varied parameter.

Comparisons among the groups were made using the appropriate statistical analysis for the data. Criterion for significance was set at $P<0.05$.

In some experiments, two-dimensional images of the heart were obtained from the left side of the animal using an HDI 3000 ultrasound system (Advanced Technology Laboratories, Bothell, Wash.) using a, 1.75 to 3.25 MHz boardband phased array transducer. During collection of the cardiac images, the ultrasound system was setup with a dynamic range of 60 dB and a linear post-processing curve. The output power was adjusted to a mechanical index of 0.2 and spatial peak time averaged of 1.1. Images were optimized using overall gain and time gain compensation at the start of the protocol and not altered during the remainder of the experiment. Image acquisition began approximately 30 seconds before injection of contrast materials and continued for about 5 minutes unless contrast disappeared before this time limit. Images were recorded on videotape.

The video images were analyzed using video densitometric techniques. Individual end-diastolic images were captured sequentially starting immediately before contrast entered the left ventricular chamber and continued for approximately one minute. Each image was digitized in a 512×480 pixel format with 256 levels of gray (O=black and 255=white) using an ImageVue™ workstation (Nova Microsonics, Mahwah, N.J.). The digitized images were imported into NIH Image v1.49 (National Institutes of Health, Washington, D.C.) for densitometric analysis.

EXPERIMENTAL EXAMPLES

Example 1

Synthesis of Methoxypolyoxyethylene(~5,000) docosamide-{DocosamidePEG(5,000), ($C_{21}$CONPEG[120])}

Docosanoic acid (0.203 g, $5.96 \times 10^{-4}$ mol, Aldrich®) was weighed into a round bottomed flask and dissolved into anhydrous chloroform (5 mL, Aldrich®) and hexanes (1 mL, Aldrich®). To the solution was added excess dicyclohexylcarbodiimide (0.15 g, $7.0 \times 10^{-4}$ mol, DCC, Aldrich®). After the solution was stirred a few minutes, an equivalent of N-hydroxysuccinimide (0.081 g, $7.0 \times 10^{-4}$ mol, Aldrich®, 97%) was added. The docosanoyl-N-succinimide ester was filtered through a small plug of glass wool contained in a pipette to remove the byproduct urea after stirring for a two hours. The N-succinimide ester was introduced directly into a concentrate of methoxypolyethylene(~5,000) amine (3.01 g, $6.0 \times 10^{-4}$ mol, Sigma®) in toluene left over from the distillation to remove any water. The reaction medium was stirred overnight under nitrogen (Air Products, High Purity Grade). The solution was refluxed for another hour. The solvents were removed by simple distillation. Dichloromethane (25 mL, Mallinckrodt, UltimaAR®) was added once the liquor had cooled. Calcium carbonate (Sigma®, ~99%) and a drop of water were mixed into the liquid. The insoluble salts were separated by filtration. TLC on silica gel (12:1; chloroform-methanol) confirmed the absence of any docosanoic acid, and the product, which remained near the origin, stained very dark in an iodine chamber. The volatile solvent was removed under reduced pressure. The white product precipitated on the addition of ethyl ether (anhydrous, Mallinckrodt, AR®) to the stirred concentrate. The product was isolated by filtration and washed with additional ethyl ether. The product was dried under vacuum. The dried powder weighed 2.56 g (80%): mp 55-61° C. $^1$H NMR (CDCl$_3$, 99.8% D, 1% TMS, Aldrich): 1.254 pp (s); 3.648 ppm (s) in a 1:12 ratio.

Example 2

Synthesis of N,N-Bis[2-(docosanoyl)oxyethyl]aminoacetic acid

Bicine (0.95 g, $5.82 \times 10^{-3}$ mol, Aldrich®, 99+%) was added to chloroform (30 mL, anhydrous, Aldrich®, 99+%). A concentrate of docosanoyl chloride, prepared by the reaction of docosanoic acid (4.12 g, $1.14 \times 10^{-2}$ mol, Aldrich®) with excess oxalyl chloride (Sigma) in chloroform, was added dropwise to the suspension. After stirring for a few minutes, excess pyridine (1.5 mL, anhydrous, Aldrich®, 99+%) was added to the flask. The flask was refluxed overnight. The reaction mixture was acidified with dilute HCl saturated with sodium chloride (Mallinckrodt, AR®). The aqueous phase was separated. Any remaining volatiles were removed from the organic phase under reduced pressure with mild heating. The glassy product was recrystallized from ethanol (Mallinckrodt, AR®). The product was recovered by filtration as an amorphous white solid. The product weighed 2.86 g after vacuum drying for a 61% yield; mp 73-75° C.; $R_f$=0.23 (silica gel, 10:1; chloroform-methanol). $^1$H NMR (CDCl$_3$, 99.8% D, 1% TMS, Aldrich): 0.880 ppm (t,); 1.254 ppm (s); IR (paraffin oil) OH 3,100 cm$^{-1}$; CO 1,760 and 1,700 cm$^{-1}$ C—O 1,180 cm$^{-1}$.

Example 3

Synthesis of 1-N',N'-Bis[2-(docosanoyl)oxyethyl] aminoacetamide-3-N-[methoxypolyethylene glycol (~5,000)], ($C_{22}$BicinePEG[120])

N,N-Bis[2-(docosanoyl)oxyethyl]aminoacetic acid (0.221 g, $2.73 \times 10^{-4}$ mol) was weighed into a round bottomed flask and dissolved into chloroform (7 mL, anhydrous, Aldrich®, 99+%). To the solution was added dicyclohexylcarbodiimide (DCC, 0.0625 g, $3.03 \times 10^{-4}$ mol, Aldrich®). After stirring for about ten minutes, N-hydroxysuccinimide (0.0345 g, $3.03 \times 10^{-4}$ mol, Aldrich®, 97%) was added. Stirring was continued for two hours. The N-hydroxysuccinimide ester was filtered through a small plug of glass wool contained in a pipette to remove the byproduct urea and introduced directly into a concentrate of methoxypolyethylene(~5,000) amine (1.52 g, $3.03 \times 10^{-4}$ mol, Sigma®) in toluene left over from the distillation to remove any water. The solution was stirred overnight under nitrogen. The solution was heated to reflux under a flow of nitrogen for one hour. The product was concentrated by removing the solvent by simple distillation. After the liquor had cooled, dichloromethane (25 mL, Mallinckrodt, UltimaAR®) was added. Calcium carbonate (0.3 g, Sigma®, ~99%) was stirred into the suspension. The insoluble salts were separated by filtration. TLC on silica gel (10:1; chloroform-methanol) confirmed the absence of any starting material and the presence of a product near the origin which stained very dark in an iodine chamber. The volatile solvent was removed under reduced pressure. The white product precipitated on the addition of anhydrous ethyl ether (75 mL, Mallinckrodt, AR®) to the stirred concentrate. The product was isolated by filtration and the cake was washed with ethyl ether. The product was dried under vacuum. The dried powder weighed 1.12 g. $^1$H NMR(CDCl$_3$, 99.8% D, 1% TMS, Aldrich): 1.254 ppm(s); 3.648 ppm(s) in a ~1:8 ratio.

Example 4

Synthesis of 1-N,N-Dioctadecylglutaramic acid

Dioctadecylamine (0.52 g, 1.0×10$^{-3}$ mol, Fluka®, >99%) was dissolved into toluene (15 mL, Mallinckrodt, AR®). Any water present was removed by simple distillation of ~5 mL of toluene. The solution was cooled to room temperature under a flow of nitrogen (Air Products, High Purity Grade) before the addition of glutaric anhydride (0.12 g, 1.0×10$^{-3}$ mol, Sigma®, ~95%). The suspension was heated until dissolved. Heating was continued for two hours. The toluene was removed by simple distillation. The product was recrystallized from acetonitrile (75 mL, Mallinckrodt, AR®). The product was recovered by filtration as a white solid. The compound weighed 0.57 g, 5.9×10$^{-4}$ mol after vacuum drying for a 89% yield; mp 57-61° C.; R$_f$=0.24 (silica gel, 12:1; chloroform-methanol). $^1$H NMR (CDCl$_3$ 99.8% D, 1% TMS, Aldrich): 0.881 ppm (t, 6H); 1.258 ppm (s, 64H); 1.478 ppm (br. s, 4H); 1.976 ppm (t, 2H); 2.457 ppm (m, 4H); 3.256 ppm (d t, 4H). IR (paraffin oil) OH 3,100 cm$^{-1}$; CO 1,720 and 1630 cm$^{-1}$ C—N 1,180 cm$^{-1}$.

Example 5

Synthesis of 1-N,N-Dioctadecyl-6-O-[methoxypolyethylene glycol (~5,000)]glutaramic acid ester, (C$_{18}$BipodPEG[120])

1-N,N-Dioctadecylglutaramic acid (0.12 g, 1.9×10$^{-4}$ mol), methoxypoly(ethylene glycol) M.W.~5,000 (1.0 g, Aldrich®) and p-toluenesulfonic acid monohydrate (0.02 g, Aldrich®) were weighed into a 100 mL round bottomed flask and dissolved into toluene (50 mL, Mallinckrodt, AR®). The flask was fitted with a Dean-Stark trap. The solution was heated to reflux under a flow of nitrogen (Air Products, High Purity Grade). Any water present was removed as an azeotrope with toluene over a four hour period. The product was concentrated by removing the solvent. After the liquor had cooled, dichloromethane (25 mL, Mallinckrodt, UltimaAR®) was added. Calcium carbonate (Sigma®, ~99%) was stirred into the suspension. The insoluble salts were separated by filtration. TLC on silica gel (12:1; chloroform-methanol) confirmed the absence of any starting material and the presence of a product near the origin which stained very dark in an iodine chamber. The volatile solvent was removed under reduced pressure. The white product precipitated on the addition of anhydrous ethyl ether (75 mL, Mallinckrodt, AR®) to the stirred concentrate. The product was isolated by filtration. The product cake was washed with ethyl ether. The product was dried under vacuum. The dried powder weighed 0.83 g. $^1$H NMR (CDCl$_3$, 99.8% D, 1% TMS, Aldrich): 1.257 ppm (s); 3.648 ppm (s) in a 1:10 ratio.

Example 6

Docosanoate, (C$_{21}$CO$_2$$^-$); Octacosanoate, (C$_{27}$CO$_2$$^-$); and DocosamidePEG(5,000), (C$_{21}$CONPEG[120]) Formulation with Perfluorobutane(s)

To a 8 dram (29.6 mL) vial was added docosanoic acid (10.0 mg, Sigma®, ~99%); octacosanoic acid (10.0 mg, Aldrich®, ~98%) and 20.0 mg of methoxypolyoxyethylene-(~5,000)docosamide weighed out on a Mettler® analytical balance. The mixture was dissolved into acetone (~1 mL, distilled Mallinckrodt Ultimar®) using mild heating. The acetone was completely removed by the application of heat under a flow of nitrogen (Air Products, High Purity Grade). Excess sodium hydrogencarbonate (~100 mg, Aldrich®, ~99.7%) was placed in the flask along with 20 mL of 25 wt. % boiled and degassed sucrose solution. The sample vial was heated to boiling (cleared) then cooled to ~60° C. The tip of the insonation probe, Heat Systems Sonicator® Ultrasonic Processor XL (Heat Systems, Inc., Farmingdale, N.Y.) Model XL 2020, in a sound box was positioned, using a small lab jack just under the surface of the liquid. A perfluorobutane(s) gas (PCR) flow (30 to 50 mL/min) was established from a lecture bottle into the bottom of the vial using micro-tubing (PVDF or equivalent) for 30 seconds. A power setting of 7 for a few seconds was applied to disperse the gas. The vial of thick white suspension of gas microbubbles was capped and allowed to cool in a room temperature water bath. A 30 c.c. plastic syringe barrel fitted with a two-way valve was filled with perfluorobutane(s). The sample was resuspended thoroughly and poured into the syringe barrel. A stopper was fitted onto the top of the syringe barrel. The sample was allowed to stand for twenty minutes. The lower 5 mL was drained into a 10 mL syringe vial filled with perfluorobutane and sealed. The sample was kept refrigerated as much as possible. Coulter® samples were taken directly from the vial after venting to the atmosphere.

The concentration, stability, size distribution, backscatter, and attenuation for this formulation were determined using the In Vitro Protocol for Acoustic Characterization described above. The results are shown in Table 1, Formulation 1.

Example 7

Octacosanoate, (C$_{27}$CO$_2$$^-$) and DocosamidePEG(5,000), (C$_{21}$CONPEG[120]) Formulation with Perfluorobutane(s)

To a 8 dram (29.6 mL) vial was added octacosanoic acid (20.0 mg, Aldrich®, ~98%) and 20.0 mg of methoxypolyoxyethylene-(~5,000)docosamide weighed out on a Mettler® analytical balance. The mixture was dissolved into acetone (~1 mL, distilled Mallinckrodt Ultimar®) using mild heating. The acetone was completely removed by the application of heat under a flow of nitrogen (Air Products, High Purity Grade). Excess sodium hydrogencarbonate (100 mg, Aldrich®, ~99.7%) was placed in the flask along with 20 mL of 25 wt. % boiled and degassed sucrose solution. The sample vial was heated to boiling (cleared) then cooled to ~60° C. Small clear oil droplets were noted on the top of the aqueous layer. The tip of the insonation probe, Heat Systems Sonicator® Ultrasonic Processor XL (Heat Systems, Inc., Farmingdale, N.Y.) Model XL 2020, in a sound box was positioned, using a small lab jack just under the surface of the liquid. The oil droplets were insonified at a power setting of 5. The suspension remained turbid after a couple of minutes of insonation. The materials would not disperse completely and were discarded.

The concentration, stability, size distribution, backscatter, and attenuation for this formulation were determined using the In Vitro Protocol for Acoustic Characterization described above. The results are shown in Table 1, Formulation 2.

Example 8

Docosanoate, ($C_{21}CO_2^-$) and DocosamidePEG(5,000), ($C_{21}CONPEG[120]$) Formulation with Perfluorobutane(s)

To a 8 dram (29.6 mL) vial was added docosanoic acid (10.0 mg, Sigma®, ~99%); octacosanoic acid (10.0 mg, Aldrich®, ~98%) and 20.0 mg of methoxypolyoxyethylene-(~5,000)docosamide weighed out on a Mettler® analytical balance. The mixture was dissolved into acetone (~1 mL, distilled Mallinckrodt Ultimar®) using mild heating. The acetone was completely removed by the application of heat under a flow of nitrogen (Air Products, High Purity Grade). Excess sodium hydrogencarbonate (~100 mg, Aldrich®, ~99.7%) was placed in the flask along with 20 mL of 25 wt. % boiled and degassed sucrose solution. The sample vial was heated to boiling (cleared) then cooled to ~60° C. The tip of the insonation probe, Heat Systems Sonicator® Ultrasonic Processor XL (Heat Systems, Inc., Farmingdale, N.Y.) Model XL 2020, in a sound box was positioned, using a small lab jack just under the surface of the liquid. A perfluorobutane(s) gas (PCR) flow (30 to 50 mL/min) was established from a lecture bottle into the bottom of the vial using micro-tubing (PVDF or equivalent) for 30 seconds. A power setting of 7 for a few seconds was applied to disperse the gas. The vial of thick white suspension of gas microbubbles was capped and allowed to cool in a room temperature water bath. A 30 c.c. plastic syringe barrel fitted with a two-way valve was filled with perfluorobutane(s). The sample was resuspended thoroughly and poured into the syringe barrel. A stopper was fitted onto the top of the syringe barrel. The sample was allowed to stand for twenty minutes. The lower 5 mL was drained into a 10 mL syringe vial filled with perfluorobutane and sealed. After standing a couple of days under refrigeration, the microenevelopes were resuspended. On microscopic examination, some aggregation of microenevelopes was noted. Clear gel aggregates were contained in the sample.

The concentration, stability, size distribution, backscatter, and attenuation for this formulation were determined using the In Vitro Protocol for Acoustic Characterization described above. The results are shown in Table 1, Formulation 3.

Example 9

Docosanoate, ($C_{21}CO_2^-$); Triacontanoate, ($C_{29}CO_2^-$); and DocosamidePEG(5,000), ($C_{21}CONPEG[120]$) Formulation with Sulfur Hexafluoride To a 8 dram (29.6 mL) vial was added docosanoic acid (10.0 mg, Sigma®, ~99%); triacontanoic acid (10.0 mg, Aldrich®, ~98%) and 24.0 mg of methoxypolyoxyethylene-(~5,000)docosamide weighed out on a Mettler® analytical balance. The mixture was dissolved into acetone (~1 mL, distilled Mallinckrodt Ultimar™) using mild heating. The acetone was completely removed by the application of heat under a flow of nitrogen (Air Products, High Purity Grade). Excess sodium hydrogencarbonate (~100 mg, Aldrich®, ~99.7%) was placed in the flask along with 10 mL of 0.9% sodium chloride solution used for irrigation (Baxter, USP). The tip of the insonation probe, Heat Systems Sonicator® Ultrasonic Processor XL (Heat Systems, Inc., Farmingdale, N.Y.) Model XL 2020, in a sound box was positioned, using a small lab jack, midway into the liquid of the vial. The intensity level of 5 was applied for 2 minutes and 30 seconds. The sample at ~70° C. was taken out of the sound box so as to cool the vial contents under a flow of tap water to a temperature of ~50° C. as measured by a FLUKE® 52 K/J thermometer fitted with a K thermocouple. The tip of the insonation horn was repositioned just under the surface of the liquid. A gas flow (30 to 50 mL/min) was established from a lecture bottle into the bottom of the vial using micro-tubing (PVDF or equivalent) at a power setting of 5 for 45 seconds and then increased to a power setting of 7 for 10 seconds. The vial of thick white suspension of gas microbubbles was capped and allowed to cool in a room temperature water bath. A 30 c.c. plastic syringe barrel fitted with a two-way valve was filled with sulfur hexafluoride, $SF_6$. The sample was resuspended thoroughly and poured into the syringe barrel. A stopper was fitted onto the top of the syringe barrel. The sample was allowed to stand for twenty minutes. The lower 5 mL was drained into a 10 mL syringe vial filled with sulfur hexafluoride, $SF_6$ and sealed. The sample was kept refrigerated as much as possible. Coulter samples were taken directly from the vial after venting to the atmosphere.

The concentration, stability, size distribution, backscatter, and attenuation for this formulation were determined using the In Vitro Protocol for Acoustic Characterization described above. The results are shown in Table 1, Formulation 4.

Example 10

Triacontanoate, ($C_{29}CO_2^-$); and DocosamidePEG(5,000), ($C_{21}CONPEG[120]$) Formulation To a 8 dram (29.6 mL) vial was added triacontanoic acid (20.0 mg, Aldrich®, ~98%) and 24.0 mg of methoxypolyoxyethylene-(~5,000)docosamide weighed out on a Mettler® analytical balance. The mixture was dissolved into acetone (~1 mL, distilled Mallinckrodt Ultimar™) using mild heating. The acetone was completely removed by the application of heat under a flow of nitrogen (Air Products, High Purity Grade). Excess sodium hydrogencarbonate (~100 mg, Aldrich®, ~99.7%) was placed in the flask along with 10 mL of 0.9% sodium chloride solution used for irrigation (Baxter, USP). The tip of the insonation probe, Heat Systems Sonicator® Ultrasonic Processor XL (Heat Systems, Inc., Farmingdale, N.Y.) Model XL 2020, in a sound box was positioned, using a small lab jack, midway into the liquid of the vial. The intensity level of 5 was applied for 3 minutes and 30 seconds. The sample did not clear after this period of insonation. Since the components were not dispersed completely, the sample was discarded.

The concentration, stability, size distribution, backscatter, and attenuation for this formulation were determined using the In Vitro Protocol for Acoustic Characterization described above. The results are shown in Table 1, Formulation 5.

Example 11

Docosanoate ($C_{21}CO_2^-$), Octacosanoate and $C_{22}$BicinePEG[120] Formulation with Sulfur Hexafluoride To a 8 dram (29.6 mL) vial was added docosanoic acid (10 mg, Sigma®, ~99%), octacosanoic acid (10 mg, Aldrich®) and 22 mg of 1-N',N'-Bis[2-(docosanoyl)oxyethyl]-aminoacetamide-N-[methoxypolyethyleneglycol(~5,000)] weighed out on a Mettler® analytical balance. The mixture was dissolved into acetone (~1 mL, distilled Mallinckrodt Ultimar™) with mild heating. The acetone was completely removed with continued mild heating under a flow of nitrogen (Air Products, High Purity Grade). Excess sodium hydrogencarbonate (~100 mg, Aldrich®, ~99.7%) was placed in the flask along with 10 mL of 0.9% sodium chloride solution used for irrigation (Baxter, USP). The tip of the insonation probe, Heat Systems Sonicator® Ultrasonic Processor XL (Heat Systems, Inc., Farmingdale, N.Y.) Model XL 2020, in a sound box was positioned, using a small lab jack, midway into the liquid of the vial. The intensity level of 5 was applied for 2 minutes and 30 seconds. The sample at ~70° C. was taken out of the sound box so as to cool the vial contents under a flow of tap water to a temperature of ~50° C. as measured by a FLUKE® 52 K/J thermometer fitted with a K thermocouple. The tip of the insonation horn was repositioned just under the surface of the liquid. A gas flow (30 to 50 mL/min) was established from a lecture bottle into the bottom of the vial using micro-tubing (PVDF or equivalent) at a power setting of 5 for 45 seconds and then increased to a power setting of 7 for 10 seconds. The vial of thick white suspension of gas microbubbles was capped and allowed to cool in a room temperature water bath. A 30 c.c. plastic syringe barrel fitted with a two-way valve was filled with sulfur hexafluoride, $SF_6$. The sample was resuspended thoroughly and poured into the syringe barrel. A stopper was fitted onto the top of the syringe barrel. The sample was allowed to stand for twenty minutes. The lower 5 mL was drained into a 10 mL syringe vial filled with sulfur hexafluoride, $SF_6$ and sealed. The sample was kept refrigerated as much as possible. Coulter samples were taken directly from the vial after venting to the atmosphere.

The concentration, stability, size distribution, backscatter, and attenuation for this formulation were determined using the In Vitro Protocol for Acoustic Characterization described above. The results are shown in Table 1, Formulation 6.

Example 12

Docosanoate ($C_{21}CO_2^-$) and $C_{22}$BicinePEG[120] Formulation with Sulfur Hexafluoride To a 8 dram (29.6 mL) vial was added docosanoic acid (20 mg, Sigma®, ~99%) and 22 mg of N,N-Bis[2-(docosanoyl)oxyethyl]aminoacetyl-N-[methoxypolyethyleneglycol (~5,000)]amide weighed out on a Mettler® analytical balance. The mixture was dissolved into acetone (~1 mL, distilled Mallinckrodt Ultimar™) with mild heating. The acetone was completely removed with continued mild heating under a flow of nitrogen (Air Products, High Purity Grade). Excess sodium hydrogencarbonate (~100 mg, Aldrich®, ~99.7%) was placed in the flask along with 10 mL of 0.9% sodium chloride solution used for irrigation (Baxter, USP). The tip of the insonation probe, Heat Systems Sonicator® Ultrasonic Processor XL (Heat Systems, Inc., Farmingdale, N.Y.) Model XL 2020, in a sound box was positioned, using a small lab jack, midway into the liquid of the vial. The intensity level of 5 was applied for 2 minutes and 30 seconds. The sample at ~70° C. was taken out of the sound box so as to cool the vial contents under a flow of tap water to a temperature of ~50° C. as measured by a FLUKE® 52 K/J thermometer fitted with a K thermocouple. The tip of the insonation horn was repositioned just under the surface of the liquid. A gas flow (30 to 50 mL/min) was established from a lecture bottle into the bottom of the vial using micro-tubing (PVDF or equivalent) at a power setting of 5 for 45 seconds and then increased to a power setting of 7 for 10 seconds. The vial of thick white suspension of gas microbubbles was capped and allowed to cool in a room temperature water bath. A 30 c.c. plastic syringe barrel fitted with a two-way valve was filled with sulfur hexafluoride, $SF_6$. The sample was suspended thoroughly and poured into the syringe barrel. A stopper was fitted onto the top of the syringe barrel. The sample was allowed to stand for twenty minutes. The lower 5 mL was drained into a 10 mL syringe vial filled with sulfur hexafluoride, $SF_6$ and sealed. The sample was kept refrigerated as much as possible. Coulter samples were taken directly from the vial after venting to the atmosphere.

The concentration, stability, size distribution, backscatter, and attenuation for this formulation were determined using the In Vitro Protocol for Acoustic Characterization described above. The results are shown in Table 1, Formulation 7.

Example 13

Octacosanoate ($C_{27}CO2^-$) and $C_{22}$BicinePEG[120] Formulation with Sulfur Hexafluoride To a 8 dram (29.6 mL) vial was added octacosanoic acid (20 mg, Sigma®, ~99%) and 22 mg of N,N-Bis[2-(docosanoyl)oxyethyl]aminoacetyl-N-[methoxypolyethyleneglycol (~5,000)]amide weighed out on a Mettler® analytical balance. The mixture was dissolved into acetone (~1 mL, distilled Mallinckrodt Ultimar™) with mild heating. The acetone was completely removed under a flow of nitrogen. Excess sodium hydrogencarbonate (~100 mg, Aldrich®, ~99.7%) was placed in the flask along with 10 mL of 0.9% sodium chloride solution used for irrigation (Baxter, USP). The tip of the insonation probe, Heat Systems Sonicator® Ultrasonic Processor XL (Heat Systems, Inc., Farmingdale, N.Y.) Model XL 2020, in a sound box was positioned, using a small lab jack, midway into the liquid of the vial. The intensity level of 5 was applied for 4 minutes and 30 seconds until the suspension cleared. The sample at ~80° C. was taken out of the sound box so as to cool the vial contents under a flow of tap water to a temperature of ~50° C. as measured by a FLUKE® 52 K/J thermometer fitted with a K thermocouple. The tip of the insonation horn was repositioned just under the surface of the liquid. A gas flow (30 to 50 mL/min) was established from a lecture bottle into the bottom of the vial using micro-tubing (PVDF or equivalent) at a power setting of 5 for 45 seconds and then increased to a power setting of 7 for 10 seconds. The vial of thick white suspension of gas microbubbles was capped and allowed to cool in a room temperature water bath. A 30 c.c. plastic syringe barrel fitted with a two-way valve was filled with sulfur hexafluoride, $SF_6$. The sample was resuspended thoroughly and poured into the syringe barrel. A stopper was fitted onto the top of the syringe barrel. The sample was allowed to stand for twenty minutes. The lower 5 mL was drained into a 10 mL syringe vial filled with sulfur hexafluoride, $SF_6$ and sealed. The sample was kept refrigerated as much as possible. Coulter samples were taken directly from the vial after venting to the atmosphere.

The concentration, stability, size distribution, backscatter, and attenuation for this formulation were determined using the In Vitro Protocol for Acoustic Characterization described above. The results are shown in Table 1, Formulation 8.

Example 14

Docosanoate ($C_{21}CO_2^-$) and $C_{18}$BipodPEG[120] Formulation with Sulfur Hexafluoride To a 8 dram (29.6 mL) vial was added 20 mg of docosanoic acid (Sigma®, ~99%) and 22 mg of 1-N,N-Dioctadecyl-6-O-[methoxypoly(ethylene glycol)5,000]glutaramic acid ester weighed out on a Mettler® analytical balance. The mixture was dissolved into acetone (~1 mL, distilled Mallinckrodt Ultimar™) with mild heating. The acetone was completely removed with continued mild heating under a flow of nitrogen (Air Products, High Purity Grade). Excess sodium hydrogencarbonate (~100 mg, Aldrich®, ~99.7%) was placed in the flask along with 10 mL of 0.9% sodium chloride solution used for irrigation (Baxter, USP). The tip of the insonation probe, Heat Systems Sonicator® Ultrasonic Processor XL (Heat Systems, Inc., Farmingdale, N.Y.) Model XL 2020, in a sound box was positioned, using a small lab jack, midway into the liquid of the vial. The intensity level of 5 was applied for 2 minutes and 30 seconds. The sample at ~70° C. was taken out of the sound box so as to cool the vial contents under a flow of tap water to a temperature of ~50° C. as measured by a FLUKE® 52 K/J thermometer fitted with a K thermocouple. The tip of the insonation horn was repositioned just under the surface of the liquid. A gas flow (30 to 50 mL/min) was established from a lecture bottle into the bottom of the vial using micro-tubing (PVDF or equivalent) at a power setting of 5 for 45 seconds and then increased to a power setting of 7 for 10 seconds. The vial of thick white suspension of gas microbubbles was capped and allowed to cool in a room temperature water bath. A 30 c.c. plastic syringe barrel fitted with a two-way valve was filled with sulfur hexafluoride, $SF_6$. The sample was suspended thoroughly and poured into the syringe barrel. A stopper was fitted onto the top of the syringe barrel. The sample was allowed to stand for twenty minutes. The lower 5 mL was drained into a 10 mL syringe vial filled with sulfur hexafluoride, $SF_6$ and sealed. The sample was kept refrigerated as much as possible. Coulter samples were taken directly from the vial after venting to the atmosphere.

The concentration, stability, size distribution, backscatter, and attenuation for this formulation were determined using the In Vitro Protocol for Acoustic Characterization described above. The results are shown in Table 1, Formulation 9.

Example 15

Octacosanoate ($C_{27}CO_2^-$) and $C_{18}$BipodPEG[120] Formulation with Sulfur Hexafluoride To a 8 dram (29.6 mL) vial was added octacosanoic acid (20 mg, Sigma®, ~99%) and 22 mg of 1-N,N-Dioctadecyl-6-O-[methoxypolyethylene glycol(~5,000)]glutaramic acid weighed out on a Mettler® analytical balance. The mixture was dissolved into acetone (~1 mL, distilled Mallinckrodt Ultimar™) with mild heating. The acetone was completely removed under a flow of nitrogen. Excess sodium hydrogencarbonate (~100 mg, Aldrich®, ~99.7%) was placed in the flask along with 10 mL of 0.9% sodium chloride solution used for irrigation (Baxter, USP). The tip of the insonation probe, Heat Systems Sonicator® Ultrasonic Processor XL (Heat Systems, Inc., Farmingdale, N.Y.) Model XL 2020, in a sound box was positioned, using a small lab jack, midway into the liquid of the vial. The intensity level of 5 was applied for 4 minutes and 30 seconds until the suspension cleared. The sample was not completely transparent since part of the material had not dispersed. The sample at ~80° C. was taken out of the sound box so as to cool the vial contents under a flow of tap water to a temperature of ~50° C. as measured by a FLUKE® 52 K/J thermometer fitted with a K thermocouple. The tip of the insonation horn was repositioned just under the surface of the liquid. A gas flow (30 to 50 mL/min) was established from a lecture bottle into the bottom of the vial using micro-tubing (PVDF or equivalent) at a power setting of 5 for 45 seconds and then increased to a power setting of 7 for 10 seconds. The vial of thick white suspension of gas microbubbles was capped and allowed to cool in a room temperature water bath. A 30 c.c. plastic syringe barrel fitted with a two-way valve was filled with sulfur hexafluoride, $SF_6$. The sample was resuspended thoroughly and poured into the syringe barrel. A stopper was fitted onto the top of the syringe barrel. The sample was allowed to stand for twenty minutes. The lower 5 mL was drained into a 10 mL syringe vial filled with sulfur hexafluoride, $SF_6$ and sealed. The sample was kept refrigerated as much as possible. Coulter samples were taken directly from the vial after venting to the atmosphere.

The concentration, stability, size distribution, backscatter, and attenuation for this formulation were determined using the In Vitro Protocol for Acoustic Characterization described above. The results are shown in Table 1, Formulation 10.

Example 16

Docosanoate ($C_{21}CO_2^-$), Octacosanoate ($C_{27}CO_2^-$) and $C_{18}$BipodPEG[120] Formulation with Sulfur Hexafluoride To a 8 dram (29.6 mL) vial was added docosanoic acid (10 mg, Sigma®, ~99%), octacosanoic acid (10 mg, Aldrich®, ~99%), and 22 mg of 1-N,N-Dioctadecyl-6-O-[methoxypoly(ethylene glycol)5,000]glutaramic acid ester weighed out on a Mettler® analytical balance. The mixture was dissolved into acetone (~1 mL, distilled Mallinckrodt Ultimar™) with mild heating. The acetone was completely removed with continued mild heating under a flow of nitrogen (Air Products, High Purity Grade). Excess sodium hydrogencarbonate (~100 mg, Aldrich®, ~99.7%) was placed in the flask along with 10 mL of 0.9% sodium chloride solution used for irrigation (Baxter, USP). The tip of the insonation probe, Heat Systems Sonicator® Ultrasonic Processor XL (Heat Systems, Inc., Farmingdale, N.Y.) Model XL 2020, in a sound box was positioned, using a small lab jack, midway into the liquid of the vial. The intensity level of 5 was applied for 2 minutes and 30 seconds. The sample at ~70° C. was taken out of the sound box so as to cool the vial contents under a flow of tap water to a temperature of ~50° C. as measured by a FLUKE® 52 K/J thermometer fitted with a K thermocouple. The tip of the insonation horn was repositioned just under the surface of the liquid. A gas flow (30 to 50 mL/min) was established from a lecture bottle into the bottom of the vial using micro-tubing (PVDF or equivalent) at a power setting of 5 for 45 seconds and then increased to a power setting of 7 for 10 seconds. The vial of thick white suspension of gas microbubbles was capped and allowed to cool in a room temperature water bath. A 30 c.c. plastic syringe barrel fitted with a two-way valve was filled with sulfur hexafluoride, $SF_6$. The sample was resuspended thoroughly and poured into the syringe barrel. A stopper was fitted onto the top of the syringe barrel. The sample was allowed to stand for twenty minutes. The lower 5 mL was drained into a 10 mL syringe vial filled with sulfur hexafluoride, $SF_6$ and sealed. The sample was kept refrigerated as much as possible. Coulter samples were taken directly from the vial after venting to the atmosphere.

The concentration, stability, size distribution, backscatter, and attenuation for this formulation were determined using the In Vitro Protocol for Acoustic Characterization described above. The results are shown in Table 1, Formulation 11.

Example 17

Docosanoate ($C_{21}CO_2^-$) and $C_{18}PEPEG[120]$ Formulation with Sulfur Hexafluoride To a 8 dram (29.6 mL) vial was added docosanoic acid (20 mg, Sigma®, ~99%) and 1,2-distearoyl-sn-glycero-3-phosphoethanolamine-N-[poly(ethylene glycol)5,000] (22 mg, Avanti Polar Lipids, Inc.) weighed out on a Mettler® analytical balance. The mixture was dissolved into anhydrous chloroform (~1 mL, Aldrich®, ~99+%) with mild heating. The chloroform was completely removed under a flow of nitrogen. Excess sodium hydrogencarbonate (~100 mg, Aldrich®, ~99.7%) was placed in the flask along with 10 mL of 0.9% sodium chloride solution used for irrigation (Baxter, USP). The tip of the insonation probe, Heat Systems Sonicator®) Ultrasonic Processor XL (Heat Systems, Inc., Farmingdale, N.Y.) Model XL 2020, in a sound box was positioned, using a small lab jack, midway into the liquid of the vial. The intensity level of 5 was applied for 2 minutes and 30 seconds. The sample at ~70° C. was taken out of the sound box so as to cool the vial contents under a flow of tap water to a temperature of ~50° C. as measured by a FLUKE® 52 K/J thermometer fitted with a K thermocouple. The tip of the insonation horn was repositioned just under the surface of the liquid. A gas flow (30 to 50 mL/min) was established from a lecture bottle into the bottom of the vial using micro-tubing (PVDF or equivalent) at a power setting of 5 for 45 seconds and then increased to a power setting of 7 for 10 seconds. The vial of thick white suspension of gas microbubbles was capped and allowed to cool in a room temperature water bath. A 30 c.c. plastic syringe barrel fitted with a two-way valve was filled with sulfur hexafluoride, $SF_6$. The sample was resuspended thoroughly and poured into the syringe barrel. A stopper was fitted onto the top of the syringe barrel. The sample was allowed to stand for twenty minutes. The lower 5 mL was drained into a 10 mL syringe vial filled with sulfur hexafluoride, $SF_6$ and sealed. The sample was kept refrigerated as much as possible. Coulter samples were taken directly from the vial after venting to the atmosphere.

The concentration, stability, size distribution, backscatter, and attenuation for this formulation were determined using the In Vitro Protocol for Acoustic Characterization described above. The results are shown in Table 1, Formulation 12.

Example 18

Octacosanoate ($C_{27}CO_2^-$) and $C_{18}PEPEG[120]$ Formulation with Sulfur Hexafluoride To a 8 dram (29.6 mL) vial was added 19.8 mg of octacosanoic acid (Sigma®, ~99%) and 22.6 mg of 1,2-distearoyl-sn-glycero-3-phosphoethanolamine-N-[poly(ethylene glycol) 5,000] (Avanti Polar Lipids, Inc.) weighed out on a Mettler® analytical balance. The mixture was dissolved into anhydrous chloroform (~1 mL, Aldrich®, 99+%) with mild heating. The chloroform was completely removed under a flow of nitrogen. Excess sodium hydrogencarbonate (~100 mg, Aldrich®, ~99.7%) was placed in the flask along with 10 mL of 0.9% sodium chloride solution used for irrigation (Baxter, USP). The tip of the insonation probe, Heat Systems Sonicator® Ultrasonic Processor XL (Heat Systems, Inc., Farmingdale, N.Y.) Model XL 2020, in a sound box was positioned, using a small lab jack, midway into the liquid of the vial. The intensity level of 5 was applied for 4 minutes and 30 seconds until the suspension cleared. The sample at ~80° C. was taken out of the sound box so as to cool the vial contents under a flow of tap water to a temperature of ~50° C. as measured by a FLUKE® 52 K/J thermometer fitted with a K thermocouple. The tip of the insonation horn was repositioned just under the surface of the liquid. A gas flow (30 to 50 mL/min) was established from a lecture bottle into the bottom of the vial using micro-tubing (PVDF or equivalent) at a power setting of 5 for 45 seconds and then increased to a power setting of 7 for 10 seconds. The vial of thick white suspension of gas microbubbles was capped and allowed to cool in a room temperature water bath. A 30 c.c. plastic syringe barrel fitted with a two-way valve was filled with sulfur hexafluoride, $SF_6$. The sample was suspended thoroughly and poured into the syringe barrel. A stopper was fitted onto the top of the syringe barrel. The sample was allowed to stand for twenty minutes. The lower 5 mL was drained into a 10 mL syringe vial filled with sulfur hexafluoride, $SF_6$ and sealed. The sample was kept refrigerated as much as possible. Coulter samples were taken directly from the vial after venting to the atmosphere.

The concentration, stability, size distribution, backscatter, and attenuation for this formulation were determined using the In Vitro Protocol for Acoustic Characterization described above. The results are shown in Table 1, Formulation 13.

Example 19

Docosanoate ($C_{21}CO_2^-$), Octacosanoate ($C_{27}CO_2^-$) and $C_{18}PEPEG[120]$ Formulation with Sulfur Hexafluoride To a 8 dram (29.6 mL) vial was added 10 mg of docosanoic acid (Sigma®, ~99%) %); 10 mg of octacosanoic acid (Aldrich®, ~98%) and 22 mg of 1,2-distearoyl-sn-glycero-3-phosphoethanolamine-N-[poly(ethylene glycol)5,000] (Avanti Polar Lipids, Inc.) weighed out on a Mettler® analytical balance. The mixture was dissolved into chloroform (~1 mL, Aldrich®, 99+%) with mild heating. The chloroform was completely removed under a flow of nitrogen. Excess sodium hydrogencarbonate (~100 mg, Aldrich®, ~99.7%) was placed in the flask along with 10 mL of 0.9% sodium chloride solution used for irrigation (Baxter, USP). The tip of the insonation probe, Heat Systems Sonicator® Ultrasonic Processor XL (Heat Systems, Inc., Farmingdale, N.Y.) Model XL 2020, in a sound box was positioned, using a small lab jack, midway into the liquid of the vial. The intensity level of 5 was applied for 2 minutes and 30 seconds. The sample at ~70° C. was taken out of the sound box so as to cool the vial contents under a flow of tap water to a temperature of ~50° C. as measured by a FLUKE® 52 K/J thermometer fitted with a K thermocouple. The tip of the insonation horn was repositioned just under the surface of the liquid. A gas flow (30 to 50 mL/min) was established from a lecture bottle into the bottom of the vial using micro-tubing (PVDF or equivalent) at a power setting of 5 for 45 seconds and then increased to a power setting of 7 for 10 seconds. The vial of thick white suspension of gas microbubbles was capped and allowed to cool in a room temperature water bath. A 30 c.c. plastic syringe barrel fitted with a two-way valve was filled with sulfur hexafluoride, $SF_6$. The sample was resuspended thoroughly and poured into the syringe barrel. A stopper was fitted onto the top of the syringe barrel. The sample was allowed to stand for twenty minutes. The lower 5 mL was drained into a 10 mL syringe vial filled with sulfur hexafluoride, $SF_6$ and sealed. The sample was kept refrigerated as much as possible. Coulter samples were taken directly from the vial after venting to the atmosphere.

The concentration, stability, size distribution, backscatter, and attenuation for this formulation were determined using the In Vitro Protocol for Acoustic Characterization described above. The results are shown in Table 1, Formulation 14.

In Vitro Results

Referring to Table 1, the microbubbles with a shell made from a blend of bipolar compounds having inter-molecular hydrophobic regions of mixed carbon chain length were more easily dispersed into the medium and more stable than the "uncorrugated" formulations. Many of the "uncorrugated" formulations would not completely disperse into the medium. Formulations 2, 3, 5 and 13 formed a thick gel or a suspension of solid particles or yielded microbubbles that aggregated on standing. Corrugated Formulations 6, 11 and 14 attenuated less between 2-5 MHz on a gas volume basis than Formulations 7, 9 and 12 that are similar but lacking the longer-chained component. Less attenuation, as evidenced by the lower number of dBs/cm at a given volume dose, allowed deeper penetration of the ultrasound signal, especially at 2 MHz. The backscatter, a measure of reflectivity, remained relatively unchanged. The net effect is that ultrasound contrast is provided without loss of imaging detail.

Figure 2A:
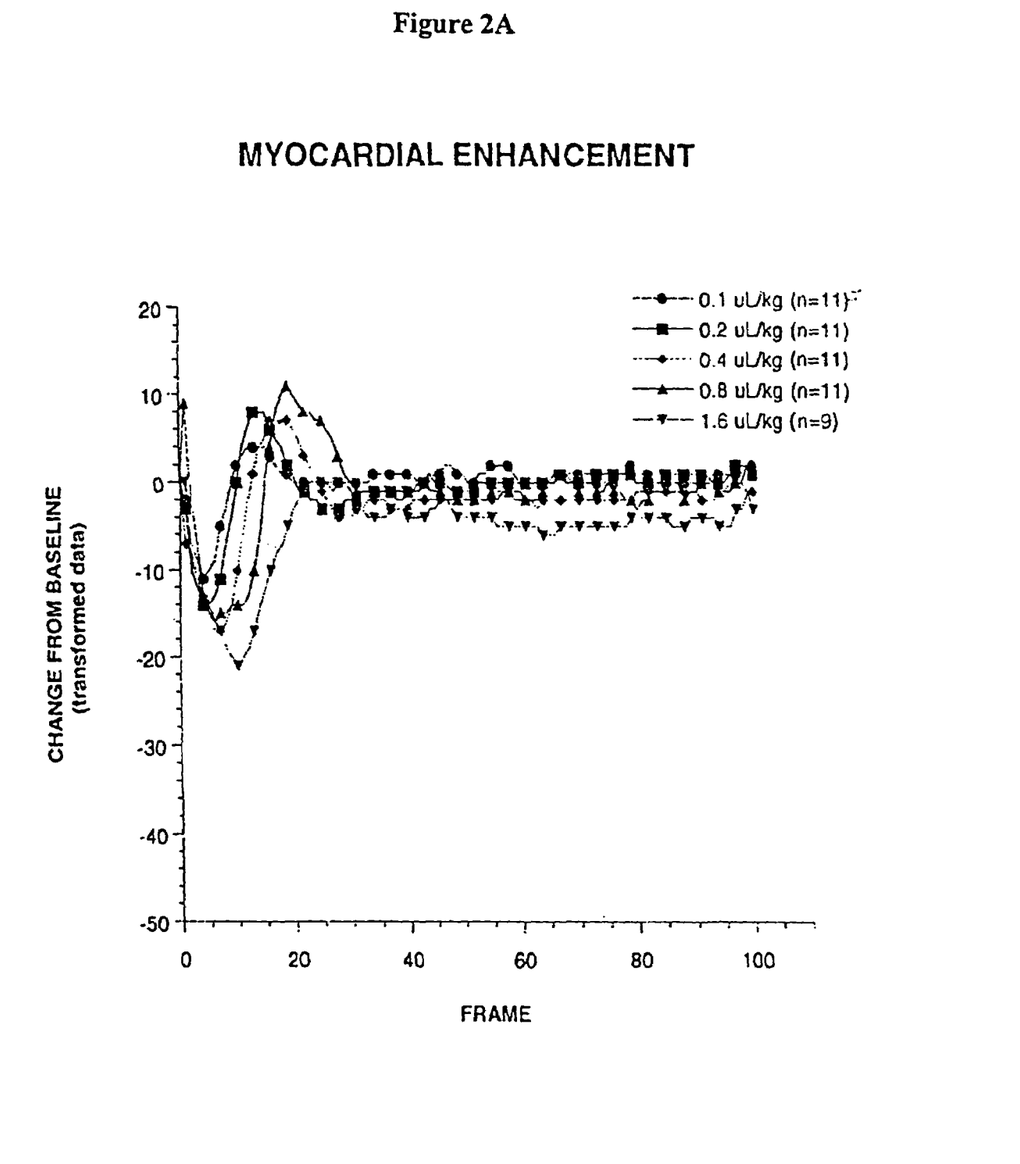
FIG. 2A shows the myocardial enhancement achieved with the formulations of the present invention.
Figure 2B:
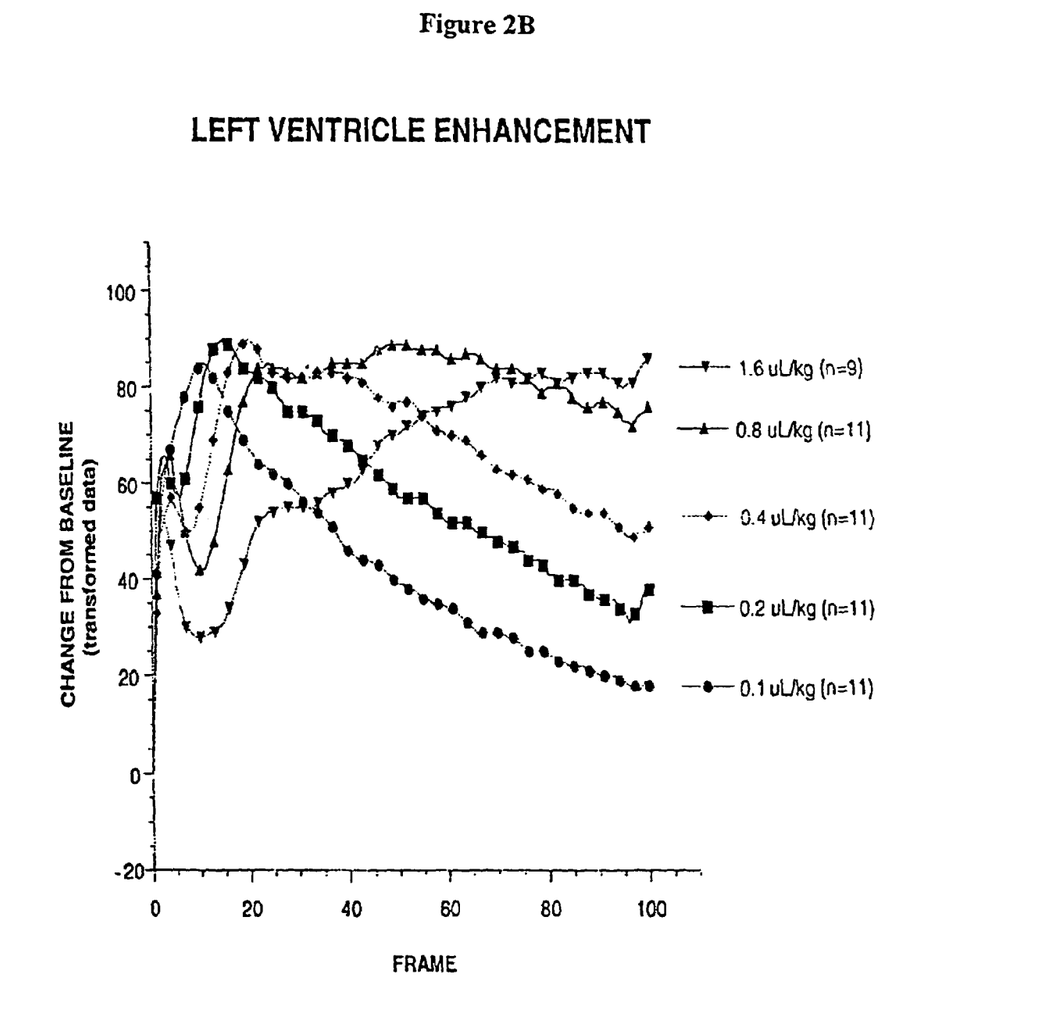
FIG. 2B shows the left ventricle enhancement achieved with the formulations of the present invention.

The experimental results show that myocardial perfusion can be observed when high concentrations of the formulation of the present invention are in the heart muscle. This in vivo experiment demonstrates that the imaging of heart perfusion is not obscured by the high concentration of microbubbles still remaining in the adjacent chambers of the heart. Other known prior art agents completely attenuate the signal and opacify the contrast anywhere in the region of the heart. As shown in FIG. 2A and FIG. 2B, image contrast is not lost with the low attenuating agent of the present invention even at relatively high concentration.

Referring to Table 1, when samples of Formulations 1, 4, and 14 are exposed to air and then diluted into aqueous media contained in a sealed flexible container, large reversible darkening of the ultrasound image with depth of field is observed with only minor pressure changes on the outside of the container. Small pressure changes can thus be calibrated against the large attenuation changes in the transmitted and reflected signal. Ultrasound imaging in conjunction with "corrugated" microbubbles can serve as a remote pressure sensors.

The "uncorrugated" formulations that were measured contained bipodal-PEG amphiphiles. Their acoustic performance was clearly inferior to the corrugated analogue as evidenced by greater attenuation in the frequency ranges of diagnostic interest. Little change was noted on the backscatter of the various samples.

Example 20

In Vivo Formulation

Docosanoate, ($C_{21}CO_2^-$); Octacosanoate, ($C_{27}CO_2^-$); and DocosamidePEG(5,000), ($C_{21}CONPEG(5,000)$) Formulation with Sulfur Hexafluoride To a 8 dram (29.6 mL) vial was added docosanoic acid (10.0 mg, Sigma®, ~99%); octacosanoic acid (10.0 mg, Aldrich®, ~98%) and 20.0 mg of methoxypolyoxyethylene-(~5,000)docosamide weighed out on a Mettler® analytical balance. The mixture was dissolved into acetone (~1 mL, distilled Mallinckrodt Ultimar®) using mild heating. The acetone was completely removed by the application of heat under a flow of nitrogen (Air Products, High Purity Grade). Excess sodium hydrogencarbonate (~100 mg, Aldrich®, ~99.7%) was placed in the flask along with 10 mL of 0.9% sodium chloride solution used for irrigation (Baxter, USP). The tip of the insonation probe, Heat Systems Sonicator® Ultrasonic Processor XL (Heat Systems, Inc., Farmingdale, N.Y.) Model XL 2020, in a sound box was positioned, using a small lab jack, midway into the liquid of the vial. The intensity level of 5 was applied for 2 minutes and 30 seconds. The sample at ~70° C. was taken out of the sound box so as to cool the vial contents under a flow of tap water to a temperature of ~50° C. as measured by a FLUKE® 52 K/J thermometer fitted with a K thermocouple. The tip of the insonation horn was repositioned just under the surface of the liquid. A gas flow (30 to 50 mL/min) was established from a lecture bottle into the bottom of the vial using micro-tubing (PVDF or equivalent) at a power setting of 5 for 45 seconds and then increased to a power setting of 7 for 10 seconds. The vial of thick white suspension of gas microbubbles was capped and allowed to cool in a room temperature water bath. A 30 c.c. plastic syringe barrel fitted with a two-way valve was filled with sulfur hexafluoride, $SF_6$. The sample was resuspended thoroughly and poured into the syringe barrel. A stopper was fitted onto the top of the syringe barrel. The sample was allowed to stand for twenty minutes. The lower 5 mL was drained into a 10 mL syringe vial filled with sulfur hexafluoride, $SF_6$ and sealed. The sample was kept refrigerated as much as possible. Coulter samples were taken directly from the vial after venting to the atmosphere.

The concentration, stability, size distribution, backscatter, and attenuation for this formulation were determined using the In Vitro Protocol for Acoustic Characterization described above. The In Vivo Protocol for Acoustic Characterization was followed for the animal data as described above. The results are shown in FIG. 2A and FIG. 2B.

Referring to FIG. 2A and FIG. 2B, myocardial perfusion reaches a maximum at around frame 20 with all except the highest dose tested. Also, the left ventricle data shows excellent enhancement for the corresponding doses. Only at the highest doses tested was some minor transient attenuation evident. The in vivo experiment demonstrates that the imaging of the heart perfusion is not obscured by a much higher concentration of microbubbles remaining in the adjacent chambers of the heart.

Both in vitro and in vivo ultrasound experiments have shown that particular molecular assemblies on the gas/liquid interface dramatically effect the acoustic efficiency of ultrasound contrast. Blends of bipolar materials containing inter-molecular hydrophobic regions of mixed chain length are highly reflective yet minimally attenuating at doses comparable those used for known contrast agents. In particular, mixtures of unbranched, long-chained alkyl, alkylether, alkylthioethers, alkyldisulfides, polyfluoroalkyl, polyfluoroalkylethers, ($C_{18}$, $C_{19}$, $C_{21}$, . . . with $C_{23}$, $C_{27}$, $C_{29}$, . . . ) carboxylic acids (salts) with a PEG conjugate(s) or other PEG-amphiphile(s) enclosing aqueous insoluble gas or gases produce stable microbubbles useful for the purposes of known agents and useful for additional indications because of the unique properties of such microbubbles.

Obviously many modifications and variations of the present invention are possible in light of the above teachings. It is therefore to be understood that within the scope of the appended claims the invention may be practiced otherwise than as specifically described.

TABLE 1

Comparative Acoustic Performance of Mixed Length Amphiphiles

| Formulation | Stable Y/N | Distribution Mean in μ | # Count Total 1 to 32μ | Vol. % Total 1 to 32μ | Backscatter (dB/cm) 2 MHz 32 | 2 MHz 128 | 5 MHz 32 | 5 MHz 128 | Attenuation (dB/cm) 2 MHz 32 | 2 MHz 128 | 5 MHz 32 | 5 MHz 128 L |
|---|---|---|---|---|---|---|---|---|---|---|---|---|
| 1. $C_{21}CO_2Na(10 C_{27}CO_2Na(10$ mg) $C_{21}CONHPEG[12$ mg) in 20 mL 25% Sucrose- | Y | 1.87 | 1.97 × E9 | 1.4% | −47 | −47 | −43 | −41 | 2 | 3 | 24 | 28 |
| 2. $C_{27}CO_2Na(20 C_{21}CONHPEG[12$ mg) in 20 mL 25% Sucrose | N*1 | — | — | — | — | — | — | — | — | — | — | — |
| 3. $C_{21}CO_2Na(20 C_{21}CONHPEG[12$ mg) in 20 mL 25% Sucrose- | N*2 | — | — | — | — | — | — | — | — | — | — | — |
| 4. $C_{21}CO_2Na(10 C_{29}CO_2Na(10$ mg) $C_{21}CONHPEG[12$ mg)/ 10 mL —$SF_6$ | Y | 1.80 | 1.77 × E9 | 0.917% | −46 | −42 | −42 | −42 | 4 | 4 | 25 | 35 |
| 5. $C_{29}CO_2Na(20 C_{21}CONHPEG[12$ 24 mg)/10 mL —$SF_6$ | N*1 | — | — | — | — | — | — | — | — | — | — | — |
| 6. $C_{21}CO_2Na(10 C_{27}CO_2Na(10$ mg) $(C_{21}CO_2)_2$Bicine-G[120](22 mg) in —$SF_6$ | Y | 1.85 | 2.06 × E9 | 1.38% | −44 | −42 | −41 | −41 | 55 | 150 | 55 | 170 |
| 7. $C_{21}CO_2Na(20(C_{21}CO_2)_2$Bicine-G[120](22 mg) in —$SF_6$ | Y | 1.80 | 2.38 × E9 | 1.30% | −46 | −44 | −42 | −43 | 60 | 161 | 89 | 270 |
| 8. $C_{27}CO_2Na(20(C_{21}CO_2)_2$Bicine-G[120](22 mg) in —$SF_6$ | N*3 | — | — | — | — | — | — | — | — | — | — | — |
| 9. $C_{21}CO_2Na(20$ mg) $(C_{18})_2NCO(CH_2)_4$ G[120](22 mg) in —$SF_6$ | Y | 1.91 | 1.43 × E9 | 0.91% | −47 | −43 | −43 | −42 | 36 | 59 | 50 | 118 |
| 10. $C_{27}CO_2Na(20$ mg) $(C_{18})_2NCO(CH_2)_4$ G[120](22 mg) in —$SF_6$ | N*3 | — | — | — | — | — | — | — | — | — | — | — |
| 11. $C_{21}CO_2Na(10 C_{27}CO_2Na(10(C_{18})_2NCO(CH_2)_4$ G[120](22 mg) in —$SF_6$ | Y | 2.15 | 1.15 × E9 | 1.10% | −51 | −47 | −42 | −41 | 3 | 7 | 24 | 62 |
| 12. $C_{21}CO_2Na(20$ mg) $C_{18}PEPEG[120](2$ n 10 mL —$SF_6$ | Y | 1.89 | 1.30 × E9 | 0.807% | −48 | −46 | −43 | −41 | 3 | 25 | 47 | 220 |
| 13. $C_{27}CO_2Na(19.8 C_{18}PEPEG[120](2)$ in 10 mL —$SF_6$ | N*4 | — | — | — | — | — | — | — | — | — | — | — |
| 14. $C_{21}CO_2Na(10$ mg) $C_{27}CO_2Na(10$ mg) $C_{18}PEPEG[120](2$ n 10 mL —$SF_6$ | Y | 2.06 | 1.09 × E9 | 0.878% | −52 | −48 | −41 | −40 | <1 | <1 | 20 | 54 |

*1 Components did not disperse after 3.5 min of insonation.
*2 Dispersed components gelled on standing.
*3 Insufficient yield of microbubbles <8 microns.
*4 Microbubbles aggregated on standing.

The invention claimed is:

1. A biocompatible composition comprising microbubbles encapsulating a gas within a shell comprising a plurality of compounds, each compound having a polar head group linked to a straight-chain hydrophobic group selected as having different chain lengths sufficient for longer chains to assemble beneath adjacent shorter chains thereby enhancing rigidity of the shell, the hydrophobic groups oriented toward the gas, wherein the compounds have the structure $R_1$—X-Z;
$R_2$—X-Z;
and $R_3$—X-Z' where $R_1$, $R_2$ and $R_3$ are hydrophobic groups selected from the group consisting of straight-chain alkyls, alkylethers, alkylthioethers, alkyldisulfides, polyfluoroalkyls, and polyfluoroalkylethers having a carbon chain length greater than or equal to 16 and less than or equal to 32 and where $R_1$ is greater than $R_2$ and $R_1$ is greater than or equal to $R_3$; $R_3$ has one or more such hydrophobic groups having the same or different lengths; X is a linker connecting the hydrophobic group to the polar head group; Z is a polar head group selected from the group consisting of $CO_2$-$M^+$, $SO_3^-M^+$, $SO_4^-M^+$, $PO_3^-M^+$, $PO_4^-M^+{}_2$, $N(R)_4{}^+$, a pyridinium or substituted pyridinium group, and a zwitterionic group; R is selected from the group consisting of —H, —$CH_3$, alkyl, cycloalkyl, substituted cycloalkyls containing one or more heteroatoms, and benzyl and can be the same or different; and Z' is a nonionic group selected from the group consisting of polysorbates, polyglycerols, polypeptides, polynucleotides, polysaccharides, polyvinylpyrrolidones, polyvinylalcohols, polyethyleneglycols, and combinations thereof.

2. The composition of claim 1 wherein $R_1$, $R_2$ and $R_3$ are straight-chain alkyl groups having from about 20 to 30 carbon atoms.

3. The composition of claim 1 wherein X is selected from the group consisting of $-(CH_2)_m-$, $-(CH_2)_m CO_2(CH_2)_n-$, $-(CH_2)_m CONH(CH_2)_n-$, $-(CH_2)_m NHCONH(CH_2)_n-$, $-(CH_2)_m OCONH(CH_2)_n-$, $-(CH_2)_m O(CH_2)_n-$, $-(CH_2)_m NH(CH_2)_n-$, $-(CH_2)_m N[(CH_2)_m]_2-$, $-(CH_2)_m S(CH_2)_n-$, $-(CH_2)_m-$, $-(CH_2)_m SO(CH_2)_n-$, $-(CH2)_m SO_2(CH_2)_n-$, $-(CH_2)_m NH(CH_2)_n CO_2(CH_2)_o-$, $-[(CH_2)_m]_2 N(CH_2)_n CONH(CH_2)_o-$, where m, n, and o are the same or different and are less than 5, DL-lysine, aspartic acid, glutamic acid, serine, cysteine, homocysteine, cystine, serinol, itaconic acid, tigilic acid, maleic acid, DL-malic acid, succinic acid, tartaric acid, malonic acid, citric acid, phthalic acid, terephthalic acid, N,N-bis[2-hydroxyethyl]-2-aminoethanesulfonic acid, N,N-bis(2-hydroxyethyl)glycine, 3-[N,N-bis(2-hydroxyethyl)amino]-2-hydroxypropanesulfonic acid, N-tris[hydroxylmethyl]methyl-3-aminopropanesulfonic acid, and N-tris[hydroxylmethyl]glycine.

4. The composition of claim 1 wherein Z' is poly(ethyleneglycol) with the number of ethyleneglycol monomer units greater than or equal to 20.

5. A method for obtaining an ultrasound contrast image of body tissue comprising:
administering into a body a biocompatible composition useful as an ultrasound contrast agent comprising microbubbles encapsulating a gas within a shell comprising a plurality of compounds, each compound having a polar head group linked to a straight-chain hydrophobic group selected as having different chain lengths sufficient for longer chains to assemble beneath adjacent shorter chains thereby enhancing rigidity of the shell, the hydrophobic groups oriented toward the gas wherein the compounds have the structure:
$R_1$—X-Z;
$R_2$—X-Z;
and $R_3$—X-Z'
where $R_1$, $R_2$ and $R_3$ are hydrophobic groups selected from the group consisting of straight-chain alkyls, alkylethers, alkylthioethers, alkyldisulfides, polyfluoroalkyls, and polyfluoroalkylethers having a carbon chain length greater than or equal to 16 and less than or equal to 32 and where $R_1$ is greater than $R_2$ and $R_1$ is greater than or equal to $R_3$; $R_3$ has one or more such hydrophobic groups having the same or different lengths; X is a linker connecting the hydrophobic group to the polar head group; Z is a polar head group selected from the group consisting of $CO_2\text{-}M^+$, $SO_3^-M^+$, $SO_4^-M^+$, $PO_3^-M^+$, $PO_4^-M^+{}_2$, $N(R)_4^+$, a pyridinium or substituted pyridinium group, and a zwitterionic group; R is selected from the group consisting of —H, —$CH_3$, alkyl, cycloalkyl, substituted cycloalkyls containing one or more heteroatoms, and benzyl and can be the same or different; and Z' is a nonionic group selected from the group consisting of polysorbates, polyglycerols, polypeptides, polynucleotides, polysaccharides, polyvinylpyrrolidones, polyvinylalcohols, polyethyleneglycols, and combinations thereof, and
taking an ultrasound image of the desired tissue.

6. The method of claim 5 wherein $R_1$, $R_2$ and $R_3$ are straight-chain alkyl groups having from about 20 to 30 carbon atoms.

7. The method of claim 5 wherein X is selected from the group consisting of $-(CH_2)_m-$, $-(CH_2)_m CO_2(CH_2)_n-$, $-(CH_2)_m CONH(CH_2)_n-$, $-(CH_2)_m NHCONH(CH_2)_n-$, $-(CH_2)_m OCONH(CH_2)_n-$, $-(CH_2)_m O(CH_2)_n-$, $-(CH_2)_m NH(CH_2)_n-$, $-(CH_2)_m N[(CH_2)_m]_2-$, $-(CH_2)_m S(CH_2)_n-$, $-(CH_2)_m-$, $-(CH_2)_m SO(CH_2)_n-$, $-(CH_2)_m SO_2(CH_2)_n-$, $-(CH_2)_m NH(CH_2)_n CO_2(CH_2)_o-$, $-[(CH_2)_m]_2 N(CH_2)_n CONH(CH_2)_o-$, where m, n, and o are the same or different and are less than 5, DL-lysine, aspartic acid, glutamic acid, serine, cysteine, homocysteine, cystine, serinol, itaconic acid, tigilic acid, maleic acid, DL-malic acid, succinic acid, tartaric acid, malonic acid, citric acid, phthalic acid, terephthalic acid, N,N-bis[2-hydroxyethyl]-2-aminoethanesulfonic acid, N,N-bis(2-hydroxyethyl)glycine, 3-[N,N-bis(2-hydroxyethyl)amino]-2-hydroxypropanesulfonic acid, N-tris[hydroxylmethyl]methyl-3-aminopropanesulfonic acid, and N-tris[hydroxylmethyl]glycine.

8. The method of claim 5 wherein Z' is poly(ethyleneglycol) with the number of ethyleneglycol monomer units greater than or equal to 20.

9. The method of claim 5 wherein the tissue is the heart and the image is a myocardial perfusion image.

* * * * *

UNITED STATES PATENT AND TRADEMARK OFFICE
CERTIFICATE OF CORRECTION

| | | |
|---|---|---|
| PATENT NO. | : 7,374,745 B2 | Page 1 of 1 |
| APPLICATION NO. | : 10/798486 | |
| DATED | : May 20, 2008 | |
| INVENTOR(S) | : Gary L. Cantrell | |

It is certified that error appears in the above-identified patent and that said Letters Patent is hereby corrected as shown below:

Column 29

Line 12, Change "2" to -- $_2$ -- at end of line.
Line 15, After "DL-" change "Iysine" to -- lysine --.

Signed and Sealed this

Sixteenth Day of September, 2008

JON W. DUDAS
*Director of the United States Patent and Trademark Office*